United States Patent [19]

Felder et al.

[11] Patent Number: 4,980,502

[45] Date of Patent: Dec. 25, 1990

[54] PARAMAGNETIC CHELATES

[75] Inventors: Ernst Felder, Riva S Vitale, Switzerland; Fulvio Uggeri, Codogno; Luciano Fumagalli; Giorio Vittadini, both of Milan, all of Italy

[73] Assignee: Bracco Industria Chimica, S.p.A., Milan, Italy

[21] Appl. No.: 411,906

[22] Filed: Sep. 25, 1989

Related U.S. Application Data

[62] Division of Ser. No. 2,115, Jan. 12, 1987, Pat. No. 4,916,246.

[30] Foreign Application Priority Data

Jan. 30, 1986 [IT] Italy ............................ 19236 A/86

[51] Int. Cl.$^5$ .......................................... C07C 229/34
[52] U.S. Cl. ................................... 562/444; 562/426; 562/556; 562/565; 562/568; 562/448
[58] Field of Search ............... 562/426, 448, 556, 565, 562/568

[56] References Cited

U.S. PATENT DOCUMENTS

| | | | |
|---|---|---|---|
| 3,028,407 | 4/1962 | Knedl et al. | 562/448 |
| 3,679,728 | 7/1972 | Morgan et al. | 562/444 |
| 4,352,751 | 10/1982 | Wieder et al. | 562/565 |
| 4,622,420 | 11/1986 | Meares et al. | 562/565 |
| 4,828,014 | 5/1989 | Baur et al. | 562/568 |

FOREIGN PATENT DOCUMENTS 723316 2/1955 United Kingdom ............... 562/565

Primary Examiner—James H. Reamer
Attorney, Agent, or Firm—Bucknam and Archer

[57] ABSTRACT

Compounds suitable for NMR imaging having the formula:

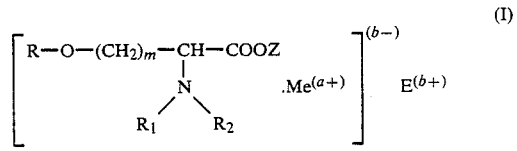

wherein
a is 2 or 3;
b is an integer from 0 to 4;
$Me^{(a+)}$ is $Fe^{(2+)}$, $Fe^{(3+)}$, $Gd^{(3+)}$, or $Mn^{(2+)}$;
$E^{(b+)}$ is an ion of an alkali metal, alkaline earth metal, alkyl ammonium, alkanol ammonium, polyhydroxyalkyl ammonium, or basic protonated amino acid, said ions representing a total charge of b;
m is an integer from 1 to 5;
R is H, alkyl with from 1 to 8 carbon atoms, alkyl with from 1 to 8 carbon atoms wherein from 1 to 5 carbons are substituted with OH; aralkyl with 1 to 4 aliphatic carbon atoms; phenyl or phenyl substituted by halogen, hydroxyl, carboxyl, carboxamide, ester, SO$_3$H, sulfonamide, lower alkyl, lower hydroxy alkyl, amino, acylamino; (poly)oxa-alkyl with 1 to 50 oxygen atoms and from 3 to 150 carbon atoms, wherein 1 to 5 hydrogen atoms may be substituted by OH; $R_1$ is the same as $R_2$ or
is —CH$_2$COOZ, —CH(CH$_3$)COOZ, CH$_2$CH$_2$—N(CH$_2$COOZ)$_2$, a hydroxy arylalkyl, hydroxy pyridylalkyl, hydroxy aryl(carboxy)alkyl or hydroxy pyridyl-(carboxyl)-alkyl radical, where the aryl or pyridyl radical may be substituted by hydroxyl, hydroxy alkyl, alkyl, halogen, carboxyl or SO$_3$H; is —CH$_2$COOZ, —CH(CH$_3$)COOZ,

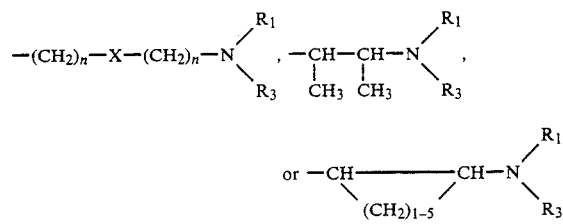

wherein
$R_3$ is —CH$_2$COOZ, —CH(CH$_3$)COOZ or a monovalent radical having the structure

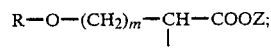

X is a direct chemical bond, —O—, —S—, 13 NH—,

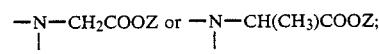

n is the integer 2 or 3, with the proviso that when X represents a direct bond, n is 1, 2 or 3;
Z is hydrogen or a unit of negative charge, and —(CH$_2$)$_m$— may also be —CH$_2$—C(CH$_3$)$_2$—.

6 Claims, No Drawings

PARAMAGNETIC CHELATES

This is a divisional of application Ser. No. 002,115, filed Jan. 12, 1987 now U.S. Pat. No. 4,916,246.

BACKGROUND OF THE INVENTION

1. Field of the Invention

The invention relates to compounds which affect the relaxation time of atomic nuclei More particularly, it pertains to compounds for use in effecting the relaxation times for nuclei in animal and human tissue which can be used for diagnosis through NMR imaging.

2. Description of the Prior Art

The NMR imaging method is based on the characteristic of certain atomic nuclei which have their own magnetic momentum and, in particular, protons, of orienting themselves, as the result of a magnetic field, in a state of equilibrium from which they can be moved by the use of pulses of a given radio frequency (resonance frequency).

The nuclei then return to their original state of equilibrium as a result of spin-spin and spin-lattice relaxation. The time required for returning to the state of equilibrium, known as relaxation time, gives valuable information on the degree of organization of the atoms and on their interaction with their environment.

On the basis of differences in proton density and relaxation times, images of biological tissues can be obtained each may be used for diagnostic purposes The greater the differences in the relaxation times of the nuclei which are present in the tissues being examined, the greater will be the contrast in the image that is obtained; cf., for example, P. Brunner et al, J. of Magnetic Resonance, 33, 83, 106 (1979).

It is known that the relaxation times of neighboring nuclei can be affected by the use of complex paramagnetic salts (G. C. Levy, et al, J. Amer. Chem. Soc. 96, 678–681 (1974)). It has therefore been proposed to administer paramagnetic ions to living organisms in order to improve the diagnostic information by the localized increase in relaxivity obtainable specifically by the use of paramagnetic substances: P. C. Lauterbur et al, Frontiers of Biol. Energetics Vo., I, 752-759 (1978); F. H. Doyle et al, Proc. of NMR Imaging Symp. held in Nashville, Tenn., U.S.A., on Oct. 26-27, 1980; J. A. Koutcher et al, J. of Nuclear Medicine 25:506–513 (1984). Various ions of transition metals and lanthanides are paramagnetic (F. A. Cotton et al., Advanced Inorganic Chemistry 1966, 634–639)

Specifically, paramagnetic ions which have a particularly strong effect on relaxation times are, for example gadolinium$^{(3+)}$, iron$^{(3+)}$, manganese$^{(2+)}$, and chromium$^{(3+)}$; cf. G. L. Wolf et al., Magnetic Resonance Annual 1985 (Raven Press, New York), 231–266.

These ions of transition metals and lanthanides are, however, too toxic for use in man: R. J. Walker, R. William "Haemochromatosis and Iron Overload", in: Iron in Biochemistry and Medicine; A. Jacobs, M. Worwood, Eds., Academic Press, London, pp. 589–613 (1974); G. G. Cotzias, "Manganese in Health and Disease", Physiol. Rev. 38, 503–532 (1958); P. Arvela, "Toxicity of Rare Earths", Prog. Pharmacol. 2, 71–114 (1979).

We have therefore an incentive to deal with this problem by trying to reduce the toxic effect of metal ions administered for diagnostic purposes by combining these ions with suitable agents: F. Hosain et al, Radiology 91, 1199–1203 (1968), describe, for example, complex compounds of diethylene triaminopentacetate (DTPA) of the lanthanide ytterbium.

Gadolinium can also be successfully detoxified by combining it, for example, with diethylene triaminopentacetic acid; but this greatly reduces the relaxivity and, therefore, the contrast-reinforcing action compared to free $Gd^{3+}$(Weinmann et al., AJR 142:619–624 (1984).

Another problem is that the compound is not always less toxic than the free ion: in the same paper, for example, Weinmann et al. report that the toxicity of the ethylenediaminotetracetic compound (EDTA) of gadolinium is higher than that of gadolinium trichloride.

The specific usefulness and tolerance of metallic complexes must therefore be individually investigated in every single case.

Weinmann reports in Physiol.Chem.Phys.Med. NMR 1984, 16, 167–172 on the pharmacokinetics of the gadolinium-DTPA complex which indicates that this complex is distributed in the organism both in the vascular space and in the considerably larger interstitium. This is a disadvantage, for example, in the imaging of blood vessels, because it requires a much larger amount of contrast medium than would be needed in the case of a contrast medium whose distribution is limited to the vascular space. See, in this respect, M. Ogan et al., "Approaches to the Chemical Synthesis of Macromolecular NMR Imaging Contrast Media for Perfusion-Dependent Enhancement", presented at the 71st Scientific Assembly and Annual Meeting RSNA, Chicago, Nov. 17-22, 1985.

Media for NMR diagnosis which contain complex paramagnetic salts of the lanthanides and transition metals are given broad coverage in European patent EP-B 71,564. Equally extensive processes for NMR diagnosis by means of complexes of lanthanides are described in EP-A 135,125 (DuPont).

Schering's European Patent No. 71 564 covers compounds of the types according to formulas I to IV:

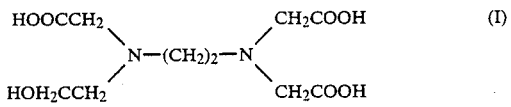

N-Hydroxyethyl-N,N',N'-ethylenediaminetriacetic acid (HEDTA)

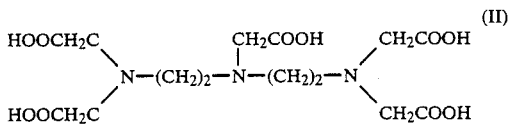

N,N,N',N'',N''-Diethylenetriaminepentaacetic acid (DTPA)

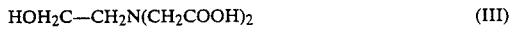

N-Hydroxyethyliminodiacetic acid

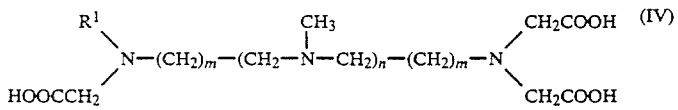

wherein
m represents 1 to 4
n represents 0 to 2
R' represents a saturated or unsaturated hydrocarbon group with 4 to 12 hydrocarbon atoms or the group —CH$_2$—COOH,
or diphosphonic acids of the general formula V

wherein
R$_2$ represents hydrogen, alkyl of 1 to 4 carbon atoms, halogen, the hydroxy—, amino— or CH$_2$—COOH groups and,
R$_3$ represents hydrogen, alkyl of 1 to 4 carbon atoms, or the —CH$_2$—COOH group, and
the ions of the lanthanide elements of numbers 57 to 70 or the ions of the transition metals of numbers 21 to 29, 42 and 44, and an organic base, by which as organic base glucamine, N-methylglucamine, N,N-dimethylglucamine, ethanolamine, diethanolamine, morpholine, lysine, ornithine and arginine are concerned, optionally with the usual additives in the art, dissolved or suspended in water or physiological salt solution characterized in that one brings into a form for oral or intravascular application, the paramagnetic complex salt dissolved or suspended in water or a physiological salt solution optionally with the usual additives in the art.

Complex compounds of iron$^{(3+)}$ and gadolinium$^{(3+)}$ for the imaging of the gastrointestinal tract are described in EP-A 124.,766.

All agents proposed up to now for NMR diagnosis, which consist of complexes of heavy metals, are not very satisfactory with regard to their practical use in man or create more or less serious problems with regard to relaxivity and tolerance. Also, they frequently exhibit insufficient selectivity of the bond with the heavy metal, insufficient stability, and particularly, lack of selective targeting to certain organs.

The tendency of many complexes to exchange the central metal ion for trace metals which are essential to the organism
or for ions, for example Ca$^{(2+)}$, which in vivo are present in relatively large amounts (cf., on this point, P. M. May, "The Present Status of Chelating Agents in Medicine", in: Progress in Medical Chemistry 20, 1983 (Elsevier Science Publ.) p. 233) ultimately limits their applicability, particularly in dosages which would be desirable for NMR diagnosis In the case of insufficient specific stability of the complex, trace metals of vital importance may, in fact, be extracted from the organism, and undesirable heavy metals, such as Gd may be deposited in their place which may remain in the organism for a long time.

Contrast media with organ specificity for NMR contrast imaging, which contain paramagnetic complexes of lanthanides, are being claimed in the published French patent application No. 2,550,449 and in EP-A 133,603. The solutions proposed there are, however, still limited and not optimal.

Therefore, there exists, now as before, a demand for contrast agents for the representation of the individual organs (for example, liver, bile ducts, spleen, pancreas, lymph nodes) and their respective anatomically pathological and functional changes.

Such paramagnetic substances for effective application in man should satisfy some or all of the following requirements:
1. A strong effect on the relaxation times T$_1$ and T$_2$ (particularly T$_1$); in other words, they should induce a high level of relaxation which, by increasing the contrast in the image, makes it possible among other things to obtain relevant information in a short amount of time with obvious advantages in terms of the economic cost of each single examination, full utilization of equipment, etc.
2. A high level of stability of the complex, both in solution and in the organism. This means that the complexing agents exhibit a high level of selectivity for the relevant paramagnetic ions as opposed to the physiological ions.
3. A distribution which is specific to the organ and the tissue in the organism.
4. An elimination kinetics which is specific to the organ and the tissue.

SUMMARY OF THE INVENTION

We have discovered compounds which meet the above-stated requirements and are particularly suited for NMR diagnostic imaging. The compounds are made up of iron$^{(2+)}$, iron$^{(3+)}$, gadolinium$^{(3+)}$, and manganese$^{(2+)}$. They are relatively simple, well tolerated, partially endowed with organ specificity and are suitable for application in nuclear spin tomograpyy. More specifically, the inventive compounds have the formula I

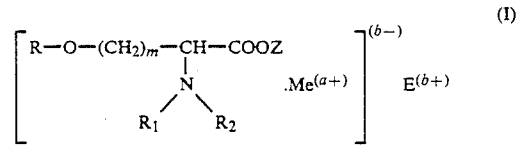

wherein
a is 2 or 3;
b is an integer from 0 to 4;
Me$^{(a+)}$ is Fe$^{(2+)}$, Fe$^{(3+)}$, Gd$^{(3+)}$, or Mn$^{(2+)}$;
E$^{(b+)}$ is an ion(s) of an alkali metal or alkaline earth metal, alkyl ammonium, alkanol ammonium, polyhydroxyalkyl ammonium, or basic protonated amino acid, with the ions representing a total charge of b units;
m is an integer from 1 to 5;
R is H, alkyl with from 1 to 8 carbon atoms, or alkyl with from 1 to 8 carbon atoms wherein from 1 to 5 carbon atoms may be substituted with OH;
is aralkyl with 1 to 4 aliphatic carbon atoms;

is phenyl or phenyl substituted by halogen, hydroxyl, carboxyl, carboxamide, ester, SO$_3$H, sulfonamide; lower alkyl (as used herein, lower alkyl means alkyl having 1 to 4 carbon atoms), or lower hydroxy alkyl, amino, acylamino;

is poly)oxa-alkyl with from 1 to 50 oxygen atoms and from 3 to 150 carbon atoms, where from 1 to 5 hydrogen atoms may be substituted by OH;

$R_1$ is the same as $R_2$ or is —CH$_2$COOZ, —CH(CH$_3$)COOZ, CH$_2$CH$_2$-N(CH$_2$COOZ)$_2$, a hydroxy arylalkyl, hydroxy pyridylalkyl, hydroxy aryl(carboxy)alkyl or hydroxy pyridyl-(carboxy)-alkyl radical, where the aryl or pyridyl radical may be substituted by hydroxyl, hydroxy alkyl, alkyl, halogen, carboxyl or SO$_3$H;

$R_2$ is —CH$_2$COOZ, —CH(CH$_3$)COOZ,

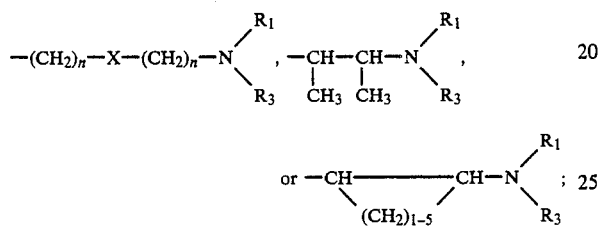

where $R_3$ is —CH$_2$COOZ, —CH(CH$_3$)COOZ or a monovalent radical of the structure

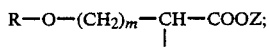

X is a simple chemical bond, i.e., no intervening atom, —O—, —S—, —NH—,

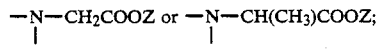

n is the integer 2 or 3, with the proviso that when X represents a simple bond, n can be 1, 2, or 3;

Z is hydrogen or a unit of negative charge, and —(CH$_2$)$_m$— may also be —CH$_2$—C(CH$_3$)$_2$—.

The compounds of the present invention may be prepared by reacting free polyamino-polycarboxylic acids having the formula

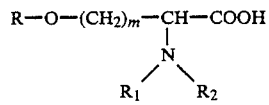

(Ia)

where R, $R_1$, $R_2$ and m have the same meaning as in formula I, or alkali metal, alkaline earth metal and/or amino salts of said acids, with salts, oxides, or hydroxides of iron$^{(2+)}$, iron$^{(3+)}$, gadolinium$^{(3+)}$, or manganese$^{(2+)}$, or with the basic salts of these metal ions.

DESCRIPTION OF THE PREFERRED EMBODIMENTS within the scope of formula I are four groups of complex heavy metal compounds having the following formulas II, III, IV and V:

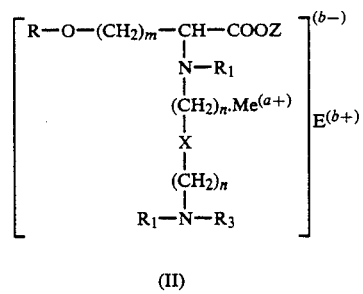

(II)

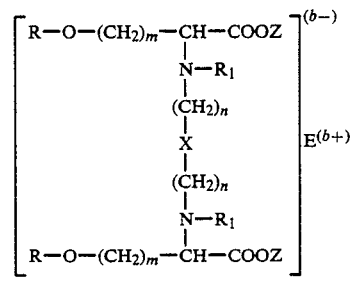

(III)

where in formulas II and III, the symbols a, b, Me$^{(a+)}$, E$^{(b+)}$, Z, R, $R_1$, $R_3$, m, n and X have the same meaning as in formula I.

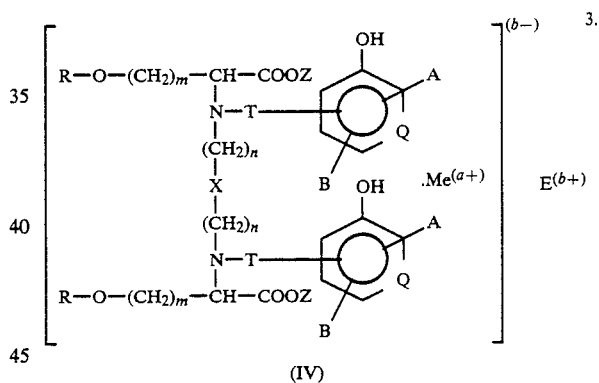

(IV)

where R, m n and X have the same meaning as defined above, T represents —(CH$_2$)$_{1-2}$, —CH(COOH)13 or —CH(COOH)CH2—, Q represents =CH— or =N—, A represents hydrogen, hydroxyl, lower hydroxy alkyl, and B represents hydrogen, lower alkyl, halogen, carboxyl or SO$_3$H. Fe$^{(3+)}$ is preferred as the metal ion.

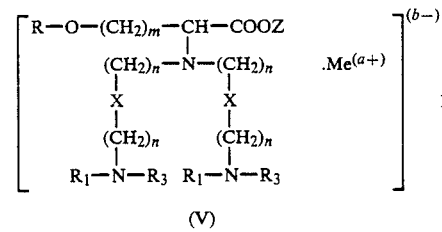

(V)

where a, b, Me$^{(a+)}$, E$^{(b+)}$, R, $R_1$, $R_3$, m, n, X and Z have the same meaning as set forth in general formula I.

The polyamino-polycarboxylic acids according to formula Ia, or their salts, which combine readily with iron, can also be caused to react directly with elemental iron to obtain the corresponding complex iron compound.

The inventive polyamino-polycarboxylic acids having formula Ia include, in particular, compounds having the following formulas:

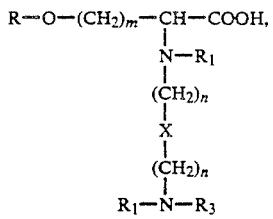
(IIa)

wherein R, $R_1$, $R_3$, m, n and X have the same meaning as in general formula I,

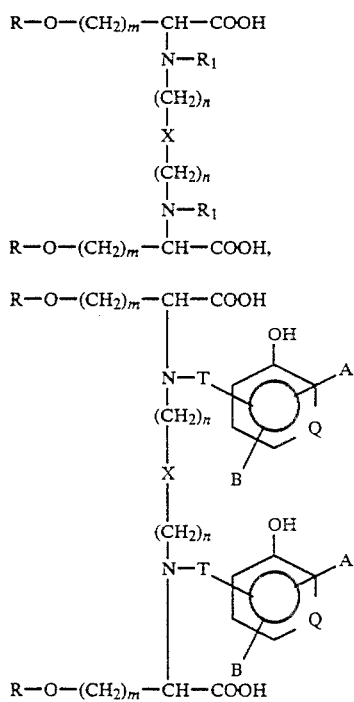

wherein T represents $-(CH_2)_{1-2}$, $-CH(COOH)-$ or $-CH(COOH)CH_2-$, Q represents $=CH-$ or $=N-$, A represents hydrogen, hydroxyl, lower hydroxy alkyl, and B represents hydrogen, lower alkyl halogen, carboxyl or $SO_3H$, and

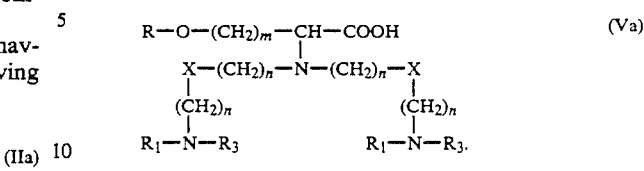
(Va)

In formulas IIa, IIIa, IVa, and Va, R, $R_1$, $R_3$, m, n and X have the same meaning as defined above.

Accordingly, the invention as disclosed herein includes:

(a) complex paramagnetic compounds of heavy metals having formula I, II, III, Iv or V;

(b) compositions for influencing the relaxation times in NMR diagnostics, containing an effective amount of at least one complex paramagnetic compound having formula I, II, III, IV or V;

(c) a procedure for the preparation of the complex heavy metal compounds having formula I, II, III, IV or V; and (d) polyamino-polycarboxylic acids having formula Ia, IIa, IIIa, IVa, or Va. The polyamino-polycarboxylic acids of the present invention may be prepared by procedures which are well known to the expert in this art. Particularly advantageous are the methods of synthesis set forth below wherein the symbols R, $R_1$, $R_2$, m, n and X have the same meaning as above defined. In addition:

CA is $-COOZ$, $-COOalkyl$, $-CONH_2$, $-CONH-R'_1$, $-CN$;

D is halogen (Cl, Br, I), $-OSO_2alkyl/aryl$, $-OSO_2Oalkyl/aryl$;

$R'_1$ is a protected group $R_1$, easily transformable into $-R_1$ by, for example, hydrolysis, hydrogenolysis, alkylation;

$R'_2$ is a protected group $R_2$, easily transformable into $-R_2$;

$R'_3$ is a protected group $R_3$, easily transformable into $-R_3$;

X' is a protected group X, easily transformable into X. (The expression "easily transformable into" means simply that the protecting group can be easily removed by conventional means to produce the corresponding desired group.)

Preparation of polyamino-polycarboxylic acids according to formula IIa, in which m=1.

Reaction schematic A

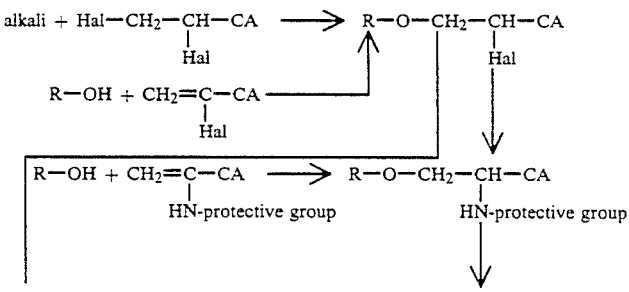

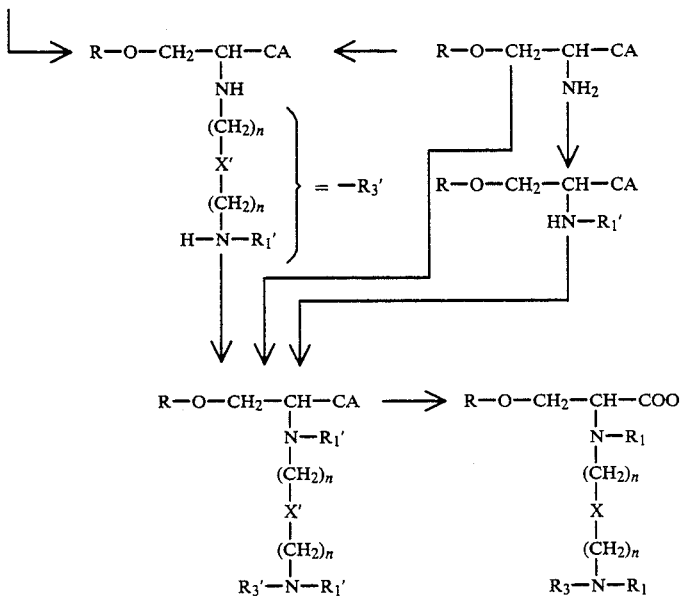
Protective groups are, for example, acyl or phenyl—CH₂—.
Preparation of polyamino-polycarboxylic acids according to general formula IIa, in which m is an integer from 1 to 5:
Reaction schematic B
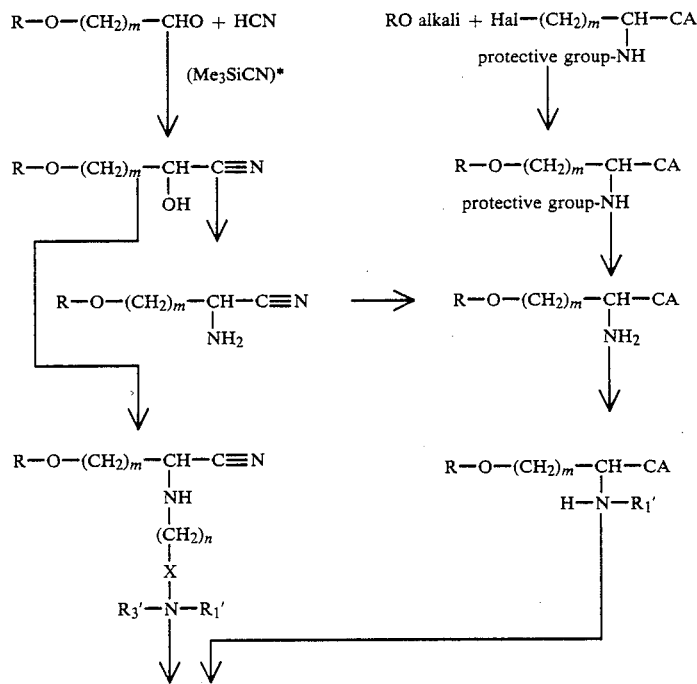

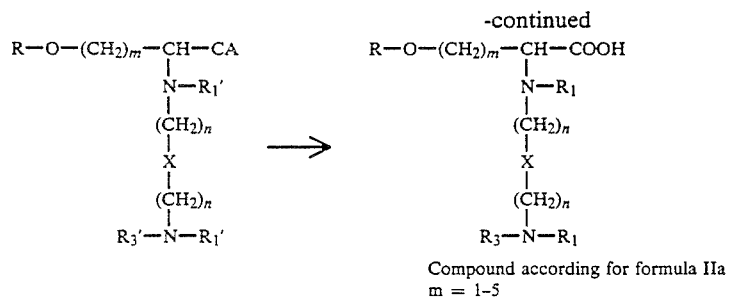

Compound according for formula IIa
m = 1–5

*Method: K. Mai et al.
Tetrahedron Letters, Vol. 25 (41), 4583–4586 (1984).

Preparation of intermediate products by the synthesis of polyamino-polycarboxylic acids having the formulas IIa and IIIa by means of imidazolidine and 2-imidazolidines as reagents Reaction schematic C

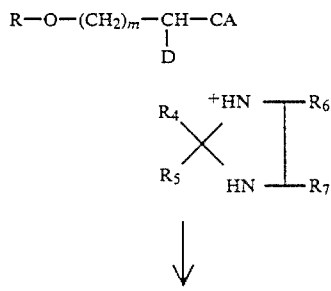

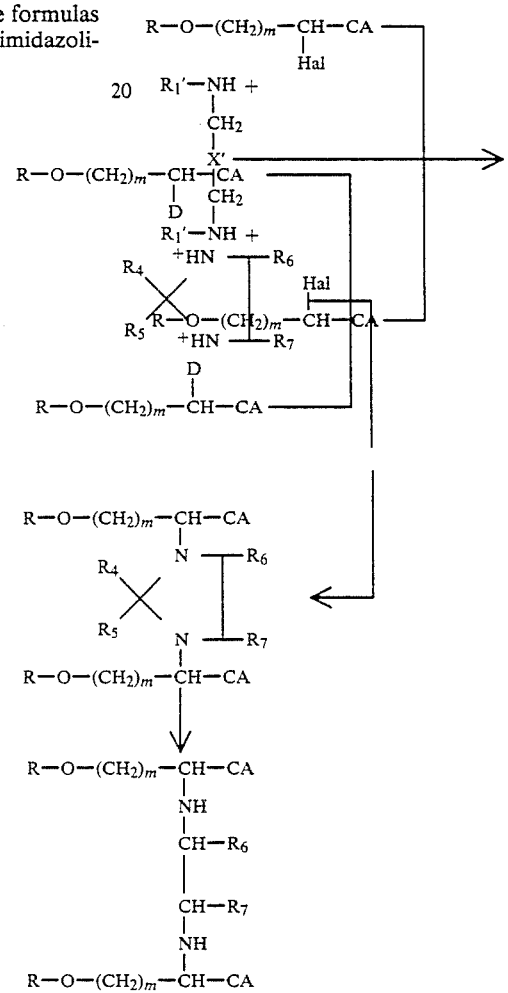

$R_4$ = H, alkyl or aryl;

$R_5$ = H, alkyl or aryl; $R_4 + R_5$ also = 0;

$R_6/R_7$ = H, alkyl ($CH_3$); $R_6 + R_7$ also = $-(CH_2)_{1-5}$;

Preparation of polyamino-polycarboxylic acids having formula IIIa, from intermediate products of syntheses A, B or C:

Reaction schematic D

Intermediate product prepared, for example, according to reaction schematic A.

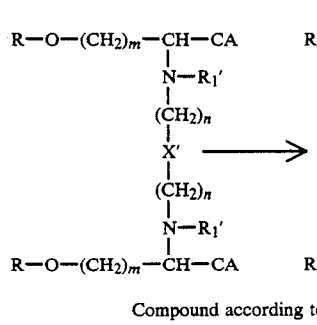
Compound according to formula IIIa.
Reaction schematic E
Intermediate product prepared, for example, according to reaction schematic A or B.
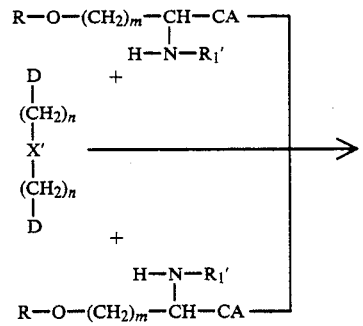
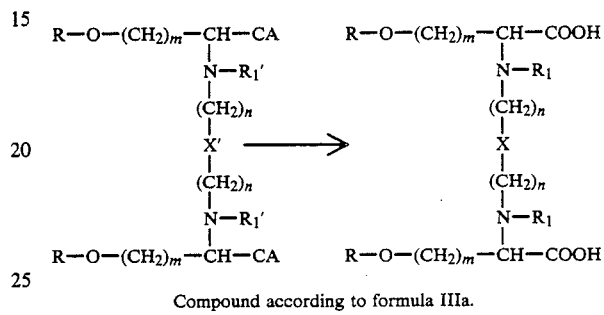
Compound according to formula IIIa.
Preparation of polyamino-polycarboxylic acids according to general formula IVa wherein T=CH$_2$.
Reaction schematic F
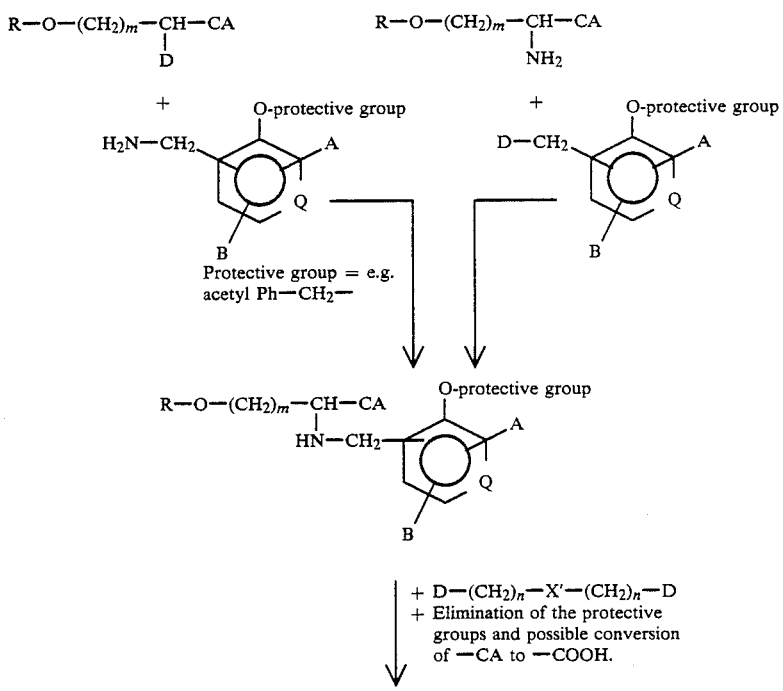

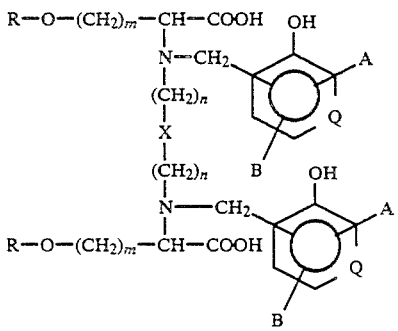

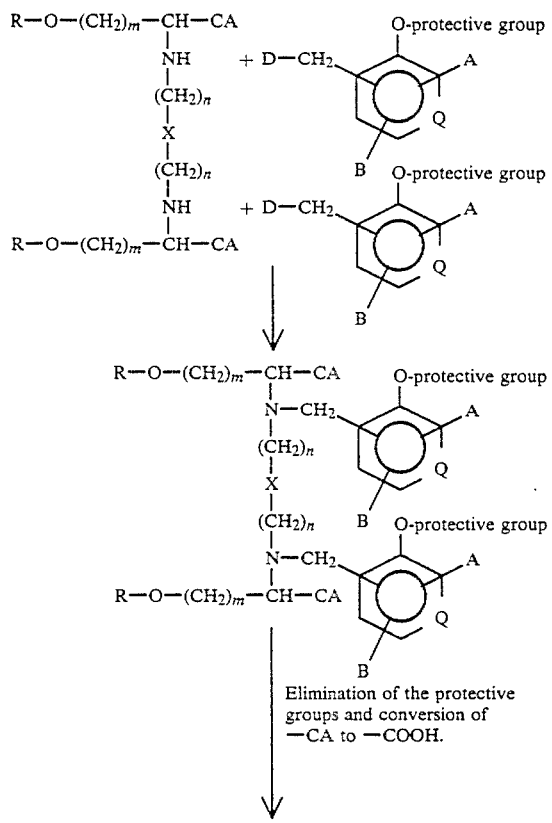

Compound according to formula IVa wherein T=CH$_2$.

Reaction schematic H

Preparation of polyamino-polycarboxylic acids according to formula Va, wherein —(CH$_2$)$_m$— may also be —CH$_2$—C(CH$_3$)$_2$—.

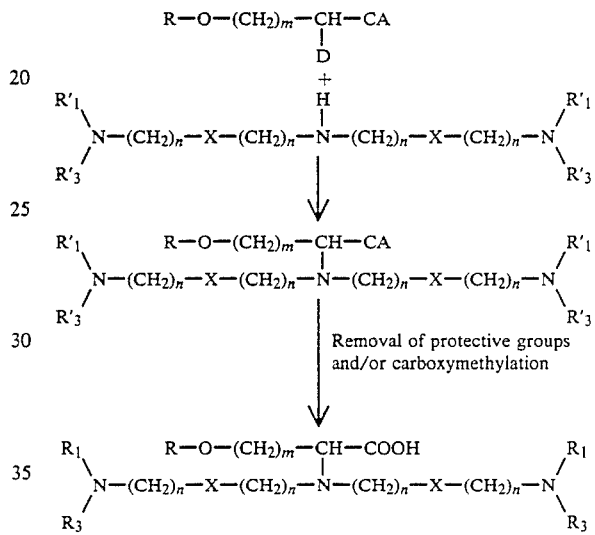

The paramagnetic compounds of iron$^{(2+)}$, iron$^{(3+)}$, gadolinium$^{(3+)}$ and manganese$^{(2+)}$ in accordance with the invention, meet the requirements for substances which enhance the contrast in nuclear spin tomography images and these compounds have a broad field of application.

The salts, which are generally water soluble, and are based on organic and inorganic compounds, can be administered intravascularly, for example, intravenously, intra-arterially, intracoronarily, intrathecally, intraperitoneally, intralymphatically, intracavitarily and intraparenchymally. Both the soluble and the less soluble compounds are suitable for oral or enteral administration, and are therefore particularly suitable for imaging of the gastrointestinal tract. Solutions or suspensions of complex salts may also be produced in aerosol form and can thus be used for aerosol bronchography.

Particularly important are the complex Fe$^{(3+)}$ compounds according to formula IV, which are distinguished by their excellent stability, good solubility and tolerability.

Certain complex compounds according to the invention have a particularly surprising organ specificity as they become concentrated, specifically in the liver, bile duct, or, after intralymphatic, intraparenchymal, intramuscular or subcutaneous administration, in the lymphatic vessels or the lymph nodes. This permits the contrast imaging of these organs.

The following examples illustrate the invention:

Preparation of the free polyamino-polycarboxylic acids

EXAMPLE 1

3-Phenylmethoxy-2-N-[2-[2-N',N'-bis-(carboxymethyl)-aminoethoxy-]-ethyl]-N-(carboxymethyl)-aminopropionic acid Formula IIa: $R=Ph-CH_2$; $m=1$; $R_1=R_332$ $-CH_2COOH$; $n=2$; $X=O$

(A) Hydrochloride of 3-phenylmethoxy-2-N-[2-(2-aminoethoxy)-ethyl]-aminopropionic acid 73.9 g of bis-2-amino-ethyl ether in 125 ml of water is reacted at 40°–60° C. with 3-phenylmethoxy-2-chloropropionic acid. The excess bis-2-amino-ethyl ether is separated as a hydrochloride. The raw product is purified by means of chromatography and finally recrystalized from ethanol. The above-captioned compound thus obtained melts at 210° C. Analysis: $Cl^{(-)}$: calculated 11.12%; measured 11.15%.

(B) 3-Phenylmethoxy-2-N-[2-[2-(N',N'-bis-carboxymethyl)-aminoethoxy]-ethyl]-(N-carboxymethyl)-aminopropionic acid 20.3 g of compound A in 60 ml of a 2N aqueous solution of sodium hydroxide is reacted with 62.5 g of bromo acetic acid at approximately 50° C. for 10–20 hours, the pH of the reaction solution being maintained at 10 by addition of 2N sodium hydroxide. This carboxymethylation reaction is repeated with another 12.5 g of bromo acetic acid and 2N NaOH. The raw product is purified by means of chromatography and recrystallization.

The compound shown in the caption forms a dihydrate which sinters at 82° C. and melts at 134° C. It is very soluble in boiling water, methanol and diluted alkali, and on the contrary, not very soluble in most organic solvents.

EXAMPLE 2

3-Phenylmethoxy-2-N-[2-N',N'-bis-(carboxymethyl)-aminoethyl]-N-(carboxymethyl)-aminopropionic acid Formula IIa: $R=Ph-CH_2$; $m=1$; $R_1=R_332$ $-CH_2COOH$; $n=1$; $X=-$

(A) Hydrochloride of 3-phenylmethoxy-2-N-(2-aminoethyl)-aminopropionic acid 130 g of 3-phenylmethoxy-2-chloropropionic acid is reacted in 1 liter of water at 50° C. with 500 ml of ethylene diamine for approximately 20 hours. The product shown in the caption is precipitated by bringing the pH to 3. Melting point: 226° C.

(B) 3-Phenylmethoxy-2-N-[2-N',N'-bis-(carboxymethyl)-aminoethyl]-N-(carboxymethyl)-aminopropionic acid 68.5 g of compound A is reacted with 209 g of bromo acetic acid in the presence of 2N aqueous sodium hydroxide at 50° C. and a pH of 9.5–10. The compound shown in the caption thus prepared is precipitated by acidification to pH 1.7. Melting point: 179°–180° C.

EXAMPLE 3

3-Hydroxy-2-N-[2-N',N'-bis-(carboxymethyl)-aminoethyl]-N-(carboxymethyl)-aminopropionic acid Formula IIa: $R=H$; $m=1$; $R_1=R_332$ $-CH_2COOH$; $n=1$; $X=-$ 20.65 g (0.05 mol) of 3-phenylmethoxy-2-N-[2-N',N'-bis-(carboxymethyl)-aminoethyl]-N-(carboxymethyl)-aminopropionic acid in 200 ml of 1N NaOH and 150 ml of water is completely hydrogenated in the presence of 38 g of palladium carbon catalyst (5% Pd). After filtering out the catalyst and evaporating until dry, the tetrasodium salt of the compound shown in the caption is obtained. Melting point: 205° C.

EXAMPLE 4

3-Phenylmethoxy-2-N-[2'-N'-[2''-N'',N''-bis-(carboxymethyl)-aminoethyl]-N'-(carboxymethyl)-aminoethyl]-N-(carboxymethyl)-aminopropionic acid Formula IIa: $R=Ph-CH_2-$; $m=1$; $R_1=R_332$ $-CH_2COOH$; $n=2$;

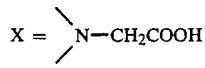

(A) 3-Phenylmethoxy-2-[2'-(2''-aminoethyl)-aminoethyl]-aminopropionic acid 42.9 g of 3-phenylmethoxy-2-chloropropionic acid (0.2 mol) is dripped under agitation into a solution of 206 g of diethylene triamine (2 mol) in 400 ml of water. The reaction mixture is agitated for 40 hours at 50° C. and then percolated through a column of strongly basic anion exchange resin. The excess amine is eliminated by washing with water.

The product is eluted from the resin with diluted 1N hydrochloric acid. The resulting solution of the trihydrochloride of 3-phenylmethoxy-2-[2'-(2''-aminoethyl)-aminoethyl]aminopropionic acid in hydrochloric acid is evaporated until dry, the residue is recovered in anhydrous ethanol and the crystallized product is filtered.

The product obtained is 62.2 g of trihydrochloride of 3-phenylmethoxy-2-[2'-(2''-aminoethyl)-aminoethyl]-aminopropionic acid (79.6% of the theoretical amount) with a melting point of 165° C.

(B) 3-Phenylmethoxy-2-N-[2'-N'-[2''-N''-bis-(carboxymethyl)-aminoethyl]-N'-(carboxymethyl)-aminoethyl]-N'-(carboxymethyl)-aminopropionic acid A solution at 50° C. of 115 g of bromo acetic acid in 413 ml of 2N aqueous sodium hydroxide is added under agitation over a period of about 30 minutes to a solution of 50 g of trihydrochloride of 3-phenylmethoxy-2-[2'-(2''-aminoethyl)aminoethyl]-aminopropionic acid in 255 ml of 2N aqueous sodium hydroxide. The pH of the reaction solution is maintained at between 9.8 and 10.2 by adding 2N aqueous sodium hydroxide. After about 8 hours, the carboxymethylation is complete. The reaction solution is percolated through a column of strongly acidic cation exchange resin and then rinsed with water. The product is eluted from the resin with 2N aqueous ammonium hydroxide. The solution thus obtained is evaporated until dry, and the evaporation residue is dissolved in water and brought to a pH of 1.7 with concentrated hydrochloric acid. The compound shown in the caption is slowly crystallized as a monohydrate.

Melting point: 118° C. Analysis after drying $C_{22}H_{31}N_3O_{11}$: calculated: C 51.45%; H 6.09%, N 8.18%; measured: C 51.28%; H 6.12%; N 8.13%.

The compound is easily soluble in hot water and ethanol and very easily soluble in alkali, amines and aqueous amino alcohols.

EXAMPLE 5

3-Hydroxy-2-N-[2'-N'-[2"-N",N"-bis-(carboxymethyl)-aminoethyl]-N'-(carboxymethyl)-aminoethyl]-N-(carboxymethyl)-aminopropionic acid Formula IIa: R=H—; m=1; $R_1=R_3$32 —$CH_2COOH$; n=2;

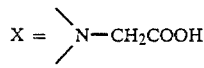

26.6 g (0.05 mol) of 3-phenylmethoxy-2-N-[2'-N'-[2"-N",N"-bis-(carboxymethyl)-aminoethyl[-N'-(carboxymethyl)-aminoethyl]-N-(carboxymethyl)-aminopropionic monohydrate acid in 250 ml of 1N sodium hydroxide and 200 ml of water is completely hydrogenated in the presence of 20 g of palladiumcarbon catalyst (5% Pd). After filtering out the catalyst and evaporating until dry, the pentasodium salt of the compound shown in the caption is obtained. Melting point: 200° C. with decomposition.

EXAMPLE 6

3-n-octyloxy-2-N-[2-N',N'-bis-(carboxymethyl)-aminoethyl]-N-(carboxymethyl)-aminopropionic acid Formula IIa: R=$CH_3$—$(CH_2)_7$—; m=1; $R_1=R_3$32 —$CH_2COOH$; n=1, X= —

(A) 3-n-octyloxy-2-chloropropionic acid:

15.2 g of metallic sodium is dissolved in 450 g of n-octanol by heating to 60° C. The sodium octylate solution thus obtained is reacted at about 50° C. with 94 g of 2,3-dichloromethyl propionate. Processing is started after 10 hours. The methyl ester of 3-n-octyloxy-2-chloropropionic acid thus obtained boils at 115°–117° C. and 0.1 mbar. It is then saponified by heating with methanolic sodium hydroxide, thereby obtaining the compound shown in the caption.

(B) Chloride of 3-n-octyloxy-2-N-(2-aminoethyl)-aminopropionic acid:

39 g of ethylene diamine is reacted over a period of 100 hours with 11.8 g of 3-n-octyloxy-2-chloropropionic acid in 150 ml of water at 40°–60° C. The excess ethylene diamine is separated as an hydrochloride. The compound shown in the caption is isolated as a hydrochloride. Melting point: 187° C.

(C) 3-n-octyloxy-2-N-[2-N',N'-bis-(carboxymethyl)-aminoethyl]-N-(carboxymethyl)-aminopropionic acid 6 g of compound (B) in a solution of aqueous sodium hydroxide is reacted with 17 g of bromo acetic acid at 50° C., with the pH of the reaction solution being maintained at 9.5–10.3 by the addition of 2N sodium hydroxide. The solution shown in the caption thus obtained is slightly soluble in water, although easily soluble in aqueous alkali. Melting point: 215° C.

EXAMPLE 7

3-methoxy-2-N-[2-(N',N'-bis-(carboxymethyl)-aminoethyl]-N-(carboxymethyl)aminopropionic acid Formula IIa: R=$CH_3$—; m=1; $R_1=R_3$32 —$CH_2COOH$; n=1; X= —

(A) Hydrochloride of 3-methoxy-2-(2-aminoethyl)-aminopropionic acid 120 g of 3-methoxy-2-chloropropionic acid is reacted for approximately 20 hours in water at 50° C., with 500 ml of ethylene diamine. The product shown in the caption is crystallized by acidification with hydrochloric acid. Melting point: 220° C.

(B) 3-methoxy-2-N-[2-N',N'-bis-(carboxymethyl)-aminoethyl]-N-(carboxymethyl)-aminopropionic acid 60 g of compound A is reacted with 220 g of bromo acetic acid in the presence of 2N aqueous sodium hydroxide at 50° C. and a pH of 9.5–10. The compound shown in the caption is precipitated by acidification at pH 1.7. Melting point: 195° C.

EXAMPLE 8

3-methoxy-2-N-[2'-N'-[2"-N",N"-bis-(carboxymethyl)-aminoethyl]-N'-(carboxymethyl)-aminoethyl]-N-(carboxymethyl)-aminopropionic acid Formula IIa: R=$CH_3$—; m=1; $R_1=R_3$32 —$CH_2COOH$; n=2;

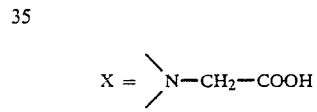

(A) 3-methoxy-2-[2'-(2"-aminoethyl)-aminoethyl]-aminopropionic acid

This compound is obtained by reaction of 3-methoxy-2-chloropropionic acid with a large excess of triethylene triamine at 50° C.

(B) 3-methoxy-2-N-[2'-N'-[2"-N",N"-bis-(carboxymethyl)-aminoethyl]-N'-(carboxymethyl)-aminoethyl]-N-(carboxymethyl)aminopropionic acid This compound is obtained by reacting compound A with bromo acetic acid in the presence of 2N aqueous sodium hydroxide at a pH of 10. Melting point: 125° C.

EXAMPLE 9

3-(2,3-dihydroxypropoxy)-2-N-[2'-N'[2"-N",N"-bis-(carboxymethyl)-aminoethyl]-N'-(carboxymethyl)aminoethyl]-N-(carboxymethyl)-aminopropionic acid Formula IIa: R=$HOCH_2CH(OH)$—$CH_2$—; m=1;

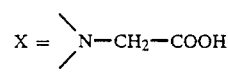

(A) 3-(2,3-dihydroxypropoxy)-2-chloropropionic acid 4-hydroxymethyl-2,2-dimethyl-1,3-dioxolane is reacted with 2,3-dichloropropionic acid to 3-(2,2-dimethyl-1,3-dioxanyl-(4)-methoxy)-2-chloropropionic acid. By treatment with hydrochloric acid, the protective group is removed and the compound shown in the caption is released.

(B)
3-(2,3-dihydroxypropoxy)-2-N-[2'-(2''-aminoethyl)-aminoethyl]-aminopropionic acid This compound is obtained by the reaction of 3-(2,3-dihydroxypropoxy)-2-chloropropionic acid with a large excess of diethylene triamine at 50° C.

(C)
3-(2,3-dihydroxypropoxy)-2-N-[2'-N'-[2''-N'',N''-bis-carboxymethyl-aminoethyl]-N-'-(carboxymethyl)-aminoethyl]-N-(carboxymethyl)-aminopropionic acid This compound is obtained by having compound. A react with bromo acetic acid in the presence of 2N sodium hydroxide at pH 10. Melting point: 140° C.

EXAMPLE 10

3-Phenoxy-2-N-[2'-N'-[2''-N'',N''-bis-(carboxymethyl)-aminoethyl]-N'-(carboxymethyl)-aminoethyl]-N-(carboxymethyl)-aminopropionic acid Formula IIa: R=phenyl; m=1; $R_1=R_332$
—CH$_2$COOH; n=2;

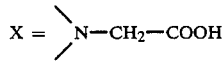

(A) 3-(phenoxy-2-N-[2'-(2''-aminoethyl)]-aminopropionic acid is obtained in a manner similar to Example 4A by means of a reaction of 3-phenoxy-2-chloropropionic acid with an excess of diethylene triamine.

(B) Compound (A) is transformed into the compound shown in the caption at pH 10 with an excess of bromo acetic acid. Melting point: 175° C.

EXAMPLE 11

3-(3,6,9-trioxadecyloxy)-2-N-[2'-N-[2''-N'',N''-bis-(carboxymethyl)-aminoethyl]-N'-(carboxymethyl)-aminoethyl]-N-(carboxymethyl)-aminopropionic acid Formula IIa: R=CH$_3$(OCH$_2$CH$_2$)$_3$—; m=1; $R_1=R_332$
—CH$_2$COOH; n=1;

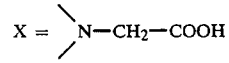

(A) 2,3-dichloropropionic acid is transformed into 3-(3,6,9-trioxadecyloxy)-2-chloropropionic acid with the sodium compound of 3,6,9-trioxadecane-1-ol.

(B) 3-(3,6,9-trioxadecyloxy)-2-N-[2'-(2''-aminoethyl)-aminoethyl]-aminopropionic acid is obtained from compound A by reaction with an excess of diethylene triamine, similar to Example 4A.

(C) Compound B is completely carboxymethylated according to the method of Example 4B and the compound shown in the caption is obtained. Melting point: 95° C.

EXAMPLE 12

N,N'-bis-(2-phenylmethoxy)-1-carboxy-1-ethyl)-N,N'-bis-(carboxymethyl)-ethylene diamine Formula IIIa: R=Ph—CH$_2$—; m=1;
$R_1$=—CH$_2$COOH; n=1; X=—

(A)
N,N'-bis-(2-phenylmethoxy)-1-carboxy-1-ethyl)-ethylene diamine 10.7 g of 3-phenylmethoxy-2-chloropropionic acid and 41.2 g of the hydrochloride of 3-phenylmethoxy-2-(2-aminoethyl)-aminopropionic acid (Example 2A) are reacted in the presence of 2N aqueous sodium hydroxide at 50° C. and pH 10. The compound shown in the caption is precipitated by acidification at a pH of 6. Melting point: 210° C.

The same compound can also be obtained by the reaction of 3-phenylmethoxy-2-chloropropionic acid with ethylene diamine or by the reaction of 3-phenylmethoxy-2-aminopropionic acid with 1,2-dibromo ethane.

(B) N,N'-bis-(2-phenylmethoxy-1-carboxy-1-ethyl)-N,N'-bis-(carboxymethyl)-ethylene diamine 13.5 g of compound (A) is reacted with 19.2 g of bromo acetic acid in the presence of 2N sodium hydroxide at 50° C. and a pH of 9.5–10. The compound shown in the caption is isolated by means of acidification and purified by recrystallization from ethanol. Melting point: 177° C.

EXAMPLE 13

N,N'-bis-(2-hydroxy-1-carboxy-1-ethyl)-N,N'-bis-(carboxymethyl)-ethylene diamine Formula IIIa: R=H; m=1; $R_1$=—CH$_2$COOH; n=1; X=—

26.63 g (0.05 mol) of N,N'-bis-(2-phenylmethoxy-1-carboxy-1-ethyl)-N,N'-bis-(carboxymethyl)-ethylene diamine in 200 ml of 1N sodium hydroxide and 150 ml water is completely hydrogenated in the presence of 38 g palladium-carbon catalyst (Pd 5%). After the catalyst has been filtered out and the compound has been evaporated until dry, the tetrasodium salt of the compound shown in the caption is obtained.

EXAMPLE 14

N,N'-bis-(2-methoxy-1-carboxy-1-ethyl)-N,N'-bis-(carboxymethyl)-ethylene diamine Formula IIIa: R=CH$_3$—; m=1; $R_1$=—CH$_2$COOH; n=1; X=—

(A) N,N'-bis-(2-methoxy-1-carboxy-1-ethyl)-ethylene diamine

A solution of 59.5 g of 3-methoxy-2-aminopropionic acid (0.5 mol) and 42 g of sodium bicarbonate (0.5 mol) in 500 ml of water is treated for 3 hours with 47 g of 1,2-dibromo ethane (0.25 mol) in 400 ml of ethanol. Simultaneously, the hydrobromic acid which is released is continually neutralized by adding an aqueous solution of 42 g of sodium bicarbonate (0.5 mol) in 500 ml of water. The solution resulting from the reaction is agitated again for 6–8 hours at 90°–95° C. and then completely evaporated; the evaporation residue is dissolved in water and the pH of the solution is adjusted to 4.1; the compound shown in the caption (14A) is crystallized in this manner.

$C_{10}H_{20}N_2O_6$ calculated: C 45.45%; H 7.63%; N 10.60%; measured C 45.13%; H 7.64%; N 10.54%.

Melting point: 240° C. with decomposition.

The NMR spectra agree with the structure indicated by the formula.

(B) N,N'-bis-(2-methoxy-1-carboxy-1-ethyl)-N,N'-bis-(carboxymethyl)-ethylene diamine 15 g of compound A is reacted at 50° C. with 30 g of bromo acetic acid at pH 10, maintained by continually adding 2N sodium hydroxide solution. The compound shown in the caption is isolated by acidification and purified by recrystallization from aqueous methanol and ethanol. Melting point: 215° C.

EXAMPLE 15

N,N'-bis-(2-(2-phenylethoxy)-1-carboxy-1-ethyl)-N,N'-bis-(carboxymethyl)-ethylene diamine Formula IIIa: R=PhCH$_2$CH$_2$—; m=1; R$_1$=—CH$_2$COOH; n=1; X=—

This compound is obtained from 3-(2-phenylethoxy)-2-hydroxypropionic acid through 3-(2-phenylethoxy)-2-(4-toluenesulfonyloxy)-propionic acid, 3-(2-phenylethoxy)-2-aminopropionic acid, 3-(2-phenylethoxy)-2-(2-aminoethyl)-aminopropionic acid, and N,N'-bis-(2-(2-phenylethoxy)-1-carboxy-1-ethyl)-ethylene diamine, in a similar manner as in Examples 1A, 2A, 12A and 12B. Melting point: 210° C.

EXAMPLE 16

N,N'-bis-(2-hydroxy-1-carboxy-1-ethyl)-N,N'-bis-(2-hydroxyphenylmethyl)-ethylene diamine Formula IVa: R=H; m=1; n=1; X=—; T=—CH$_2$—; A=B=H; Q=—CH=

(A) N,N'-bis-(2-phenylmethoxy-1-carboxy-1-ethyl)-N,N'-bis-(2-phenylmethoxy-phenylmethyl)-ethylene diamine N,N'-bis-(2-phenylmethoxy-1-carboxy-1-ethyl)-ethylene diamine, prepared according to Example 2A, is reacted in ethanol in the presence of 2N NaOH at a pH of approximately 10 and at 40°–80° C. with 2-(phenylmethoxy)-phenyl-methyl chloride.

(B) N,N'-bis-(2-hydroxy-1-carboxy-1-ethyl)-N,N-bis-(2-hydroxyphenylmethyl)-ethylene diamine This compound is obtained by catalytic hydrogenation of A in a manner similar to that of Example 13.

EXAMPLE 17

N,N'-bis-(2-methoxy-1-carboxy-1-ethyl)-N,N'-bis-(2-hydroxyphenylmethyl)-ethylene diamine Formula IVa: R=CH$_3$; m=1; n=1; T=—CH$_2$; A=B=H; Q=—CH=; X=—

Into a hot solution at 40° C. of 26.4 g of N,N'-bis-(2-methoxy-1-carboxy-1-ethyl)-ethylene diamine (0.1 mol) in 95 ml of ethanol and 100 ml of 2N aqueous sodium hydroxide a solution of 49.5 g of 2-acetoxy-phenylmethyl bromide (0.216 mol) in 195 ml of ethanol is dripped for about 2 hours, adjusting the pH, and 211 ml of 2N aqueous sodium hydroxide is dripped for about 9 hours. The pH is maintained between 9.8 and 10 by controlling the addition of NaOH.

Then the product is extracted with ethyl ether, the pH is adjusted to 8 by adding hydrochloric acid, and the product is extracted again with ethyl ether. The aqueous phase is evaporated to an oil. The residue is placed in water and acidified with hydrochloric acid. The precipitated raw product is dissolved in diluted sodium hydroxide; the solution is adjusted to a pH of 5 and purified by fractionation on an adsorbent made of a polymerized acrylic ester base. The compound shown in the caption, which is precipitated by acidification with hydrochloric acid at a pH of 1.8, melts at approximately 140° C.

$C_{24}H_{32}N_2O_8$ calculated: C 60.49%; H 6.77%; N 5.88%; measured: C 60.61%; H 6.47%; N 5.87%.

The NMR spectra agree with the structure indicated.

EXAMPLE 18

N,N'-bis-(2-hydroxy-1-carboxy-1-ethyl)-N,N'-bis-(2-hydroxyphenylmethyl)-ethylene diamine Formula IVa: R=H; m=1; n=1; X=—; T=—CH$_2$—; A=B=H; Q=—CH=

A mixture of 4.7 g N,N'-bis-(2-methoxy-1-carboxy-1-ethyl)-N,N'-bis-(2-hydroxy-phenylmethyl)-ethylenediamine (Example 17), 16 g trimethyl silyl iodide (0.08 mol), 6.32 g pyridine (0.08 mol) in 10 ml of chloroform is stirred at room temperature overnight, under nitrogen. The reaction mixture is filtered and the solvent evaporated in vacuo. The residue is poured in water giving a solid that after purification by chromatography furnishes N,N'-bis-(2-hydroxy-1-carboxy-1-ethyl)-N,N'-bis-(2-hydroxy-phenylmethyl)-ethylene diamine.

EXAMPLE 19

N,N'-bis-(3,6,9,12-tetraoxa-1-carboxy-1-tridecyl)-N,N'-bis-(2-hydroxyphenylmethyl)-ethylene diamine Formula IVa: R=CH$_3$(OCH$_2$CH$_2$)$_3$—; m=1; T=—CH$_2$—; n=1; X=—; A=B=H; Q=—CH=

(A) 3-(3,6,9-trioxadecyloxy)-2-aminopropionic acid

This product is obtained with a melting point of 184°–185° C. and a yield of 70% by treatment of 3-(3,6,9-trioxadecyloxy)-2-chloropropionic acid (Ex. 11A) with 25% ammonia (1 mol/3.5 mol) at 115° C. for two hours and removal of the salts by passage through an ion exchange resin column.

(B) N,N'-bis-(3,6,9,12-tetraoxa-1-carboxy-1-tridecyl)-ethylene diamine 3.2 g (17 mmol) of 1.2-dibromo ethane in 27 ml of ethanol and 2.85 g of sodium bicarbonate in 30 ml of water are dripped simultaneously into a solution of 8.5 g (34 mmol) of product 19A) and 2.85 g (34 mmol) of sodium bicarbonate in 35 ml of water, agitated at 90° C. After maintaining the mixture at 90° C. for 2 hours, the ethanol is removed and the remaining solution is passed through an acidic-type cation exchange resin. The title compound is eluated by aqueous ammonia. The eluate obtained produces by concentration and crystallization from ethanol N,N'-bis-(3,6,9,12-tetraoxa-1-carboxy-1-tridecyl)-ethylene diamine with a melting point of 192° C.

(C) The product of Example 19B) is treated with 2-acetoxyphenylmethyl bromide in the same manner as described in Example 17, to obtain N,N'-bis-(3,6,9,12- tetraoxa-1-carboxy-1-tridecyl)-N,N'-bis-(2-hydroxy-phenylmethyl)-ethylene diamine. Melting point 190° C.

EXAMPLE 20

4-methoxy-3,3-dimethyl-2-N-(2-N',N'-bis-(carboxymethyl)-aminoethyl]-N-(carboxymethyl)-aminobutyric acid Formula IIa: R=CH$_3$—;
—(CH$_2$)$_m$—=—CH$_2$C(CH$_3$)$_2$—;
R$_1$=R$_3$=—CH$_2$COOH; n=1; X=—

(A)
4-methoxy-3,3-dimethyl-2-N-(2-aminoethyl)-aminobutyric acid

From 3-hydroxy-2,2-dimethyl propionaldehyde, 4-methoxy-3,3-dimethyl-2-aminobutyric acid is prepared by the conventional method. From the latter, by reaction with an excess of chloro acetonitrile in dimethyl acetamide, 4-methoxy-3,3-dimethyl-2-N-(cyanomethyl)-aminobutyric acid is obtained. By hydrogenation in the presence of a palladium-carbon catalyst and in the presence of ammonia, 4-methoxy-3,3-dimethyl-2-N-(2-aminoethyl)-aminobutyric acid is obtained.

(B)
4-methoxy-3,3-dimethyl-2-N-[2'-N',N'-bis-(carboxymethyl)-aminoethyl]-N-(carboxymethyl)-aminobutyric acid The product of Example 20A is completely carboxymethylated with bromo acetic acid and the compound shown in the caption is thus obtained. Melting point: 155° C.

EXAMPLE 21

3-methoxy-2-N,N-bis-[2-N',N'-bis-(carboxymethyl)-aminoethyl]aminopropionic acid

Formula Va: R=CH$_3$—; m=1; n=1; X=—; R$_1$=R$_3$32 —CH$_2$COOH (A) 3-methoxy-2-bromo-propionitrile (0.1 mol) is reacted in dimethyl acetamide (DMA), at 100°-125° C. and in the presence of potassium carbonate with 0.13 mol of bis-(2-acetylaminoethyl) amine. The 3-methoxy-2-N,N-bis-(2-acetylaminoethyl)-aminopropionitrile obtained is saponified in ethanolic sodium hydroxide, with the ethanol being gradually distilled and substituted step by step by water. 3-methoxy-2-N,N-bis-(2-aminoethyl)-aminopropionic acid is thus obtained.

(B) 3-methoxy-2-N,N-bis-(2-aminoethyl)-aminopropionic acid is subjected to complete carboxymethylation with an excess of bromo acetic acid and in the presence of sodium hydroxide at a pH of approximately 10. The compound shown in the caption is thus formed. Melting point: 170° C.

EXAMPLE 22

4-methoxy-3,3-dimethyl-2-N,N-bis-[2-N',N'-bis-(carboxymethyl)-aminoethyl]-aminobutyric acid Formula Va: R=CH$_3$—;
—(CH$_2$)$_m$—=—CH$_2$—C(CH$_3$)$_2$—; n=1; X=—;
R$_1$=R$_3$32 —CH$_2$COOH;

(A) 4-methoxy-3,3-dimethyl-2-hydroxy butyric acid is prepared by conventional methods from 3-hydroxy-2,2-dimethyl-propionaldehyde and from that compound the ethyl ester of 4-methoxy-3,3-dimethyl-2-bromo-butyric acid is obtained.

(B) The ethyl ester of 4-methoxy-3,3-dimethyl-2-bromo-butyric acid (0.1 mol) is reacted in anhydrous dimethyl acetamide, at 100°-125° C. and in the presence of potassium carbonate, with 0.13 mol of bis-[2-N,N-bis-(ethoxycarbonylmethyl)-aminoethyl]amine. The ethyl ester of 4-methoxy-3,3-dimethyl-2-N,N-bis-[2-N',N'-bis-(ethoxycarbonylmethyl)-aminoethyl]-aminobutyric acid is saponified by heating in ethanolic sodium hydroxide, and the compound shown in the caption is obtained.

Melting point: 175° C.

In a similar manner, the polyamino-polycarboxylic acids listed in the following tables are obtained.

Polyamino-polycarboxylic acids according to formula IIa:

| No. | R | R$_1$ | R$_3$ | m | n | X |
|-----|---|-------|-------|---|---|---|
| 1 | CH$_3$(CH$_2$)$_7$— | —CH$_2$COOH | —CH$_2$COOH | 1 | 2 | 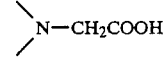 |
| 2 | CH$_3$(CH$_2$)$_9$— | —CH$_2$COOH | —CH$_2$COOH | 1 | 2 | 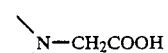 |
| 3 | CH$_3$(CH$_2$)$_{11}$— | —CH$_2$COOH | —CH$_2$COOH | 1 | 2 |  |

-continued

| No. | R | $R_1$ | $R_3$ | m | n | X |
|---|---|---|---|---|---|---|
| 4 | $CH_3(CH_2)_{15}-$ | $-CH_2COOH$ | $-CH_2COOH$ | 1 | 2 | $-(OCH_2CH_2)_2-O-$ |
| 5 | $Ph-CH_2-CH_2-$ | $-CH_2COOH$ | $-CH_2COOH$ | 2 | 2 | $\diagdown N-CH_2COOH \diagup$ |
| 6 | 4-Chlor-Ph-$CH_2-$ | $-CH_2COOH$ | $-CH_2COOH$ | 1 | 1 | — |
| 7 | Ph-$CH_2-$ | $-CH(CH_3)COOH$ | $-CH(CH_3)COOH$ | 1 | 1 | — |
| 8 | Ph-$CH_2-$ | $-CH(CH_3)COOH$ | $-CH(CH_3)COOH$ | 1 | 2 | S |
| 9 | Phenyl-(≡Ph—) | $-CH_2COOH$ | $-CH_2COOH$ | 1 | 1 | — |
| 10 | 4-HOOC-Ph— | $-CH_2COOH$ | $-CH_2COOH$ | 1 | 2 | $\diagdown N-CH_2COOH \diagup$ |
| 11 | $CH_3(OCH_2CH_2)_{\sim 11}-$ | $-CH_2COOH$ | $-CH_2COOH$ | 1 | 1 | — |
| 12 | $CH_3(OCH_2CH_2)_{\sim 11}-$ | $-CH_2COOH$ | $-CH_2COOH$ | 2 | 1 | — |
| 13 | $HO-CH_2C(CH_2OH)_2CH_2-$ | $-CH_2COOH$ | $-CH_2COOH$ | 2 | 1 | — |
| 14 | $H(OCH_2CH-CH_2)_{\sim 4}-$<br>           $\|$<br>           OH | $-CH_2COOH$ | $-CH_2COOH$ | 2 | 1 | — |
| 15 | $HOCH_2(CHOH)_4CH_2-$ | $-CH_2COOH$ | $-CH_2COOH$ | 1 | 2 | $\diagdown N-CH_2COOH \diagup$ |
| 16 | $HOCH_2(CHOH)_4CH_2-$ | $-CH_2COOH$ | $-CH_2COOH$ | 2 | 2 | $\diagdown N-CH_2COOH \diagup$ |
| 17 | $CH_3(OCH_2CH_2)_6-$ | $-CH_2COOH$ | $-CH_2COOH$ | )[1] | 2 | $\diagdown N-CH_2COOH \diagup$ |

)[1] = $-(CH_2)_m = -CH_2-(CH_3)_2-$

Polyamino-polycarboxylic acids according to formula IIIa

| No. | R | $R_1$ | m | n | X |
|---|---|---|---|---|---|
| 1 | $C_2H_5-$ | $-CH_2COOH$ | 2 | 2 | S |
| 2 | $(CH_3)_2CH-$ | $-CH_2COOH$ | 1 | 2 | $\diagdown N-CH_2COOH \diagup$ |
| 3 | Ph-$CH_2-$ | $-CH_2COOH$ | )[1] | 2 | O |
| 4 | $H(OCH_2CH_2)_8-$ | $-CH_2COOH$ | )[1] | 2 | O |
| 5 | $CH_3(OCH_2CH_2)_4-$ | $-CH_2COOH$ | )[1] | 1 | — |
| 6 | $H(OCH_2CH_2)_2-$ | $-CH_2COOH$ | 1 | 1 | — |
| 7 | $H(OCH_2CH_2)_2-$ | $-CH_2COOH$ | 1 | 2 | $\diagdown N-CH_2COOH \diagup$ |
| 8 | $H(OCH_2CH_2)_4-$ | $-CH_2COOH$ | 1 | 1 | — |
| 9 | $H(OCH_2CH_2)_{\sim 11}-$ | $-CH_2COOH$ | 2 | 2 | $\diagdown N-CH_2COOH \diagup$ |
| 10 | $HOCH_2(CHOH)_4CH_2-$ | $-CH_2COOH$ | 1 | 1 | — |

-continued

| No. | R | $R_1$ | m | n | X |
|---|---|---|---|---|---|
| 11 | $HOCH_2(CHOH)_4CH_2-$ | $-CH_2COOH$ | 2 | 2 | $\diagdown N-CH_2COOH \diagup$ |

$)^1 = -(CH_2)_m = -CH_2-C(CH_3)_2-$

Polyamino-carboxylic acids according to formula IVa

Polyamino-carboxylic acids according to formula IIa

| No. | R | T | Position of —OH | Q | A | B | m | n | X |
|---|---|---|---|---|---|---|---|---|---|
| 1 | H | $-CH_2-$ | 2 | $-CH=$ | 3OH— | H | 1 | 1 | — |
| 2 | H | $-(CH_2)_2-$ | 2 | $-CH=$ | 3OH— | H | 1 | 1 | — |
| 3 | H | $-CH_2-$ | 2 | $-CH=$ | H | 5 $HOSO_2-$ | 1 | 1 | — |
| 4 | $HOCH_2CH(OH)CH_2-$ | $-CH_2-$ | 4 | $-CH=$ | H | H | 1 | 1 | — |
| 5 | $CH_3OCH_2CH_2-$ | $-CH_2-$ | 2 | $-CH=$ | H | H | 2 | 1 | — |
| 6 | $CH_3(OCH_2CH_2)_4-$ | $-CH_2-$ | 3 | $-CH=$ | H | 5-$CH_3O-$ | 1 | 1 | — |
| 7 | $CH_3-CH_2CH_2-$ | $-CH_2-$ | 2 | $-CH=$ | 3OH— | H | 1 | 1 | — |
| 8 | $CH_3OCH_2CH_2-$ | $-CH(COOH)-$ | 2 | $-CH=$ | H | H | 2 | 2 | O |
| 9 | $CH_3OCH_2CH_2-$ | $-CH-CH_2-$<br>$\quad\mid$<br>$\quad COOH$ | 2 | $-CH=$ | 4 Cl— | H | 1 | 1 | — |
| 10 | $CH_3OCH_2CH_2-$ | 4-$CH_2-$ | 3 | $-N=$ | 2 $CH_3-$ | 5 $HOCH_2-$ | 1 | 1 | — |
| 11 | $CH_3OCH_2CH_2-$ | 4-$CH_2-$ | 3 | $-N=$ | 2 $CH_3-$ | 5 $HOCH_2-$ | 2 | 2 | O |
| 12 | $CH_3(OCH_2CH_2)_3-$ | 4-$CH_2-$ | 3 | $-N=$ | 2 $CH_3-$ | 5 $HOCH_2-$ | 2 | 2 | O |
| 13 | $CH_3(CH_2)_{11}-$ | $-CH_2-$ | 2 | $-CH=$ | 4 HOOC— | H | 1 | 2 | O |

| No. | R | $R_1$ | $R_3$ | $-(CH_2)_n-X-(CH_2)_n-$ | m |
|---|---|---|---|---|---|
| 1 | $PhCH_2-$ | $-CH_2COOH$ | $-CH_2COOH$ | $-CH-CH-$<br>$\;\mid\quad\mid$<br>$CH_3\;CH_3$ | 1 |
| 2 | $CH_3(OCH_2CH_2)_6-$ | $-CH_2COOH$ | $-CH_2COOH$ | $-CH\!-\!-\!-\!-\!-\!CH-$<br>$\;\diagdown\quad\quad\diagup$<br>$\;\;\;(CH_2)_4$ | $)^1$ |
| 3 | $CH_3-$ | $-CH_2COOH$ | $-CH_2COOH$ | $-CH-CH-$<br>$\;\mid\quad\mid$<br>$CH_3\;CH_3$ | 1 |
| 4 | DEGL— | $-CH_2COOH$ | $-CH_2COOH$ | $-CH-CH-$<br>$\;\mid\quad\mid$<br>$CH_3\;CH_3$ | 1 |

DEGL = 1 deoxy-1-glucityl-
$^1$: $(CH_2)_m = -CH_2-C(CH_3)_2-$

Polyamino-carboxylic acids according to formula IVa T=$-CH_2-$

Polyamino-carboxylic acids according to formula IIIa

| No. | R | Position of —OH | Q | A | B | m | n | X |
|---|---|---|---|---|---|---|---|---|
| 14 | $CH_3-$ | 2 | $-CH=$ | H | H | $-CH_2C(CH_3)_2-$ | 1 | — |
| 15 | $H(OCH_2CH_2)_7-$ | 2 | $-CH=$ | H | H | $-CH_2C(CH_3)_2-$ | 1 | — |
| 16 | $HOCH_2CH(OH)CH_2-$ | 2 | $-CH=$ | H | H | $-CH_2C(CH_3)_2-$ | 1 | — |
| 17 | $CH_3-$ | 2 | $-CH=$ | 5—$CH_3O-$ | H | $-CH_2C(CH_3)_2-$ | 1 | — |
| 18 | H— | 5 | 3—$N=$ | 4—$CH_3$ | 6—$CH_2OH$ | $-CH_2C(CH_3)_2-$ | 1 | — |
| 19 | Ph—$CH_2-$ | 5 | 3—$N=$ | 4—$CH_3$ | 6—$CH_2OH$ | $-CH_2C(CH_3)_2-$ | 1 | — |

| No. | R | $R_1$ | $-(CH_2)_n-X-(CH_2)_n-$ | m |
|---|---|---|---|---|
| 1 | $CH_3-$ | $-CH_2COOH$ | $-CH-CH-$<br>$\;\mid\quad\mid$<br>$CH_3\;CH_3$ | 1 |

-continued

| No. | R | R₁ | —(CH$_2$)$_n$—X—(CH$_2$)$_n$— | m |
|---|---|---|---|---|
| 2 | CH$_3$— | —CH$_2$COOH | —CH—CH—<br>    \|    \|<br>   CH$_3$ CH$_3$ | 2 |
| 3 | CH$_3$— | —CH$_2$COOH | —CH————CH—<br>   \\       /<br>    (CH$_2$)$_4$ | )¹ |
| 4 | Ph- | —CH$_2$COOH | —CH————CH—<br>   \\       /<br>    (CH$_2$)$_4$ | 1 |
| 5 | CH$_3$(OCH$_2$CH$_2$)$_4$— | —CH$_2$COOH | —CH—CH—<br>    \|    \|<br>   CH$_3$ CH$_3$ | )¹ |

)¹ —(CH$_2$)$_m$ = —CH$_2$—C(CH$_3$)$_2$—

Polyamino-carboxylic acids according to formula Va

| No. | R | R₁ | R₃ | m | n | X |
|---|---|---|---|---|---|---|
| 1 | Ph- | —CH$_2$COOH | —CH$_2$COOH | 2 | 2 | \N—CH$_2$COOH / |
| 2 | Ph- | —CH$_2$COOH | —CH$_2$COOH | 3 | 2 | \N—CH$_2$COOH / |
| 3 | CH$_3$— | —CH$_2$COOH | 2 HO—Ph-CH$_2$— | 2 | 1 | — |
| 4 | CH$_3$— | —CH$_2$COOH | 2.3-(HO)$_2$Ph-CH$_2$— | 2 | 1 | — |
| 5 | PhCH$_2$— | —CH$_2$COOH | —CH$_2$COOH | 1 | 1 | — |
| 6 | 4-H$_2$N—Ph-CH$_2$— | —CH$_2$COOH | —CH$_2$COOH | )¹ | 1 | — |
| 7 | CH$_3$(OCH$_2$CH$_2$)$_6$— | —CH$_2$COOH | —CH$_2$COOH | )¹ | 1 | — |

)¹ = —(CH$_2$)$_m$ = —CH$_2$—C(CH$_3$)$_2$—

Preparation of the complex compounds according to general formula I (or formulas II to V, respectively) from the polyamino-polycarboxylic acids according to general formulas Ia (or formulas IIa to Va, respectively) which are the basis of these complex compounds and of ready-made solutions for use as contrast-enhancing substances according to the invention.

EXAMPLE 23

Complex manganese compound of 3-phenylmethoxy-2-N-[2-N',N'-bis-(carboxymethyl)-aminoethyl]-N-(carboxymethyl)-aminopropionic acid Formula II: Me$^{(a+)}$=Mn$^{(2+)}$; b=2; E=2H; R=Ph—CH$_2$—; m=1, n=1; R$_1$=R$_3$=—CH$_2$COO$^{(-)}$; Z=$^{(-)}$; X=—.

49.2 g of 3-phenylmethoxy-2-N-[2-N',N'-bis-(carboxymethyl)-aminoethyl]-N-(carboxymethyl)-aminopropionic acid (=the compound shown in the caption of Example 2) (0.119 mol) and 13.67 g of manganese carbonate (0.119 mol) are heated in 1100 ml of water at 100° C. under agitation. After about 20 minutes a pinkish-red solution is formed which loses color completely after an additional 10 minutes. The reaction mixture is maintained at about 100° C. for one and one-half hours, then filtered until clear and evaporated in a vacuum until dry. The complex manganese compound thus obtained melts, in a dehydrated condition, at 156°-158° C. Analysis of the dehydrated compound: C$_{18}$H$_{22}$MnN$_2$O$_9$:

calculated: C 46.46%; H 4.76%; N 6.02% Mn 11.80%;

measured: C 45.82%; H 4.81%; N 6.11%, Mn 11.52%.

EXAMPLE 24

Salt of tris-(hydroxymethyl)-aminomethane (TRIS) of the complex manganese compound shown in Example 23

Formula II: Me$^{(a+)}$=Mn$^{(2+)}$; b=2; E$^{(b+)}$=2.(H$_3$N—C(CH$_2$OH)$_3$)$^+$; R=Ph—CH$_2$—; m=1; n=1; R$_1$=R$_3$=—CH$_2$COO$^{(-)}$; Z=$^{(-)}$; X=—.

To a hot solution, at 60° C., of 28 g of tris-(hydroxymethyl)-aminomethane in 500 ml of double-distilled water suitable for injection is added, under agitation, 41.28 g (0.1 mol) of 3-phenylmethoxy-2-N-[2-N',N'-bis-(carboxymethyl)-aminoethyl]-N-(carboxymethyl)-aminopropionic acid. The solution thus obtained is treated with 11.48 g of manganese carbonate (0.1 mol) and agitated at 60° C. until completely dissolved. The clear solution is diluted with 1000 ml of double-distilled water and then filtered under sterile conditions.

A number of the characteristics of the compound obtained are listed in Tables 1 and 2.

UV spectrum: lambda max.=256 nm; epsilon=239.

The sterile clear solution is cooled to −30° C. and then freeze-dried at 0.01 torr and +28° C. The freeze-dried product is filled under sterile conditions into 14 serum vials. When it is to be used, the solution is reconstituted by injecting it with 10 ml of double-distilled water. The amount of solution obtained is a sufficient amount of contrast-enhancing agent for nuclear-spin tomography of one adult.

EXAMPLE 25

N-methyl-glucamine salt of the complex manganese compound according to Example 23

Formula II: $Me^{(a+)}=Mn^{(2+)}$; b=2; $E^{(b+)}=2.(CH_3NH_2CH_2(CHOH)_5H)^+$; R=Ph—$CH_2$—; m=1; n=1; $R_1=R_3$=—$CH_2COO^{(-)}$; Z=$^{(-)}$; X=—

(A) A suspension of 206.4 g of 3-phenylmethoxy-2-N-[2-N',N'-bis-(carboxymethyl)-aminoethyl]-N-(carboxymethyl)-aminopropionic acid (0.5 mol) in 600 ml of double-distilled water is treated in portions with 204.6 g of N-methyl-D-glucamine. The solution obtained with a pH of about 5, is slowly treated, under agitation, with 200 ml of a 2.5 molar solution of manganese chloride (0.5 mol). Each time a gaseous precipitate is formed which begins to dissolve under agitation. After the entire MnCl$_2$ solution has been added, the pH of the solution is brought to 6.5–7.0 by the addition of N-methyl-D-glucamine. The solution is diluted to a volume of 1000 ml and filtered in sterile conditions.

UV spectrum: lambda max.=225 nm; epsilon=235.

(B) The same complex salt is also obtained in the following manner: 46.5 g of the complex manganese compound obtained according to Example 23 is dissolved in 600 ml of double-distilled water and a solution with a pH of about 2 is obtained. The pH of the solution is then adjusted to 6.5–7.0 by adding N-methyl-D-glucamine. The solution is diluted to a volume of 1000 ml and filtered in sterile conditions. UV spectrum: lambda max.=225 nm; epsilon=235.

The solutions obtained according to (A) or (B) can be used to enhance the contrast of the images obtained by nuclear spin tomography.

Dosage

Solution A—approximately 15 ml
Solution B—approximately 70 ml

EXAMPLE 26

The sodium salt of the complex gadolinium compound of
3-phenyl-methoxy-2-N-[2'-N'-[2''-N'',N''-bis-(carboxymethyl)-aminoethyl]-N'-(carboxymethyl)-aminoethyl]-N-(carboxymethyl)-aminopropionic acid Formula II: $Me^{(a+)}=Gd^{(3+)}$; b=2; $E^{(b+)}=2\ Na^{(+)}$; Z=$^{(-)}$; R=Ph—$CH_2$—; m=1; n=2; $R_1=R_3$=—$CH_2COO^{(-)}$;

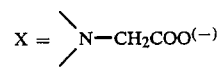

16 g of sodium hydroxide is gradually added to a suspension of 53.15 g of 3-phenylmethoxy-2-N-[2'-N'-[2''-N'',N''-bis-(carboxymethyl)-aminoethyl]-N'-(carboxymethyl)-aminoethyl]-N-(carboxymethyl)-aminopropionic monohydrate acid (the compound shown in the caption of Example 4) in 500 ml of double-distilled water. The solution obtained is slowly treated under agitation with 200 ml of a 0.5 molar solution of gadolinium chloride and simultaneously with as much of a 2N solution of sodium hydroxide as is needed to maintain the pH of the reaction solution between 4.5 and 6.0.

Once the addition of gadolinium chloride is completed, the pH of the solution is adjusted to 6.5–7.0, the solution is diluted to 1000 ml and filtered in sterile conditions in a nitrogen atmosphere.

UV spectrum: lambda=256 nm; epsilon=220.

The solution is transferred into serum vials in sterile conditions or is freeze-dried.

Dosage: 20–200 ml (0.2–2.4 ml per kg of body weight).

EXAMPLE 27

TRIS salt of the complex gadolinium compound of
3-phenylmethoxy-2-N-[2'-N'-[2''-N'',N''-bis-(carboxymethyl)-aminoethyl]-N-(carboxymethyl)-aminoethyl]-N-(carboxymethyl)-aminopropionic acid Formula II: $Me^{(a+)}=Gd^{(3+)}$; b=2; $E^{(b+)}=2.(H_3NC(CH_2OH)_3)^+$; Z=$^{(-)}$; R=Ph—$CH_2$; m=1; n=2; $R_1=R_3$=—$CH_2COO^{(-)}$;

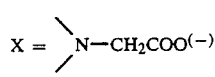

28 g of TRIS is gradually added to a suspension of 53.15 g of 3-phenylmethoxy-2-N-[2'-N'-[2''-N'',N''-bis-(carboxymethyl)-aminoethyl]-N'-(carboxymethyl)-aminoethyl]-N-(carboxymethyl)-aminopropionic acid in 500 ml of double-distilled water suitable for injection.

The solution obtained is slowly treated under agitation with 200 ml of a 0.5 molar solution of gadolinium chloride and simultaneously with TRIS (=tris-(hydroxymethyl)-aminomethane), in order to maintain the pH of the solution between 4.5 and 6.0. After the entire quantity of GdCl$_3$ has been added, the pH is adjusted to 6.5–7.0 by adding TRIS, the solution is diluted to 1000 ml, filtered in sterile conditions and transferred to serum vials or freeze-dried.

UV spectrum: lambda=256 nm; epsilon=208.

EXAMPLE 28

Serinol salt of the complex gadolinium compound of
3-phenylmethoxy-2-N-[2'-N'-[2''-N'',N''-bis(carboxymethyl)-aminoethyl]-N'-(carboxymethyl)-aminoethyl]-N-(carboxymethyl)-aminopropionic acid Formula II: $Me^{(a+)}=Gd^{(3+)}$; b=2; $E^{(b+)}=2.(H_3NCH(CH_2OH)_2)^{(+)}$; Z=$^{(-)}$; R=Ph—$CH_2$—; m=1; n=2; $R_1=R_3$=—$CH_2COO^{(-)}$;

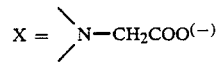

The preparation is similar to that of Example 27 with the TRIS being replaced by an equimolar amount of serinol (=1,3-dihydroxy-2-aminopropane).

UV spectrum: lambda=256 nm; epsilon=232.

EXAMPLE 29

The L-ornithine salt of the complex gadolinium compound of 3-phenylmethoxy-2-N-[2'-N'-[2''-N'',N''-bis-(carboxymethyl)-aminoethyl]-N'-(carboxymethyl)-aminoethyl]-N-(carboxymethyl)-aminopropionic acid Formula II: $Me^{(a+)} = Gd^{(3+)}$; $b=2$;
$E^{(b+)} = 2.(H_3N(CH_2)_3CH(NH_2)COOH)^{(+)}$; $Z=^{(-)}$;
$R=Ph-CH_2-$; $m=1$; $n=2$; $R_1 = R_3 = -CH_2COO^{(-)}$;

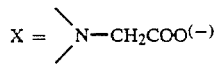

The preparation is similar to that of Example 27, with the tris being replaced by an equimolar amount of L-ornithine. The corresponding lysine salt is obtained in the same manner.

EXAMPLE 30

The N-methylglucamine salt of the complex iron compound N,N'-bis-(2-methoxy-1-carboxy-1-ethyl)-N,N'-bis(2-hydroxyphenylmethyl)-ethylene diamine Formula IVa: $Me^{(a+)} = Fe^{(3+)}$; $b=1$;
$E^{(b+)} = (CH_3NH_2CH_2(CHOH)_4CH_2OH)^{(+)}$;
$R=CH_3-$; $m=1$; $n=1$; $T=-CH_2-$; $A=B=H$;
$Q=-CH=$; $Z=^{(-)}$ To a suspension of 3.336 g of N,N'-bis-(2-methoxy-1-carboxy-1-ethyl)-N,N'-bis-(2-hydroxyphenylmethyl)-ethylene diamine (7 mmol) in 50 ml of water "for injection", 14 ml of an aqueous 1M solution of N-methylglucamine is added with which the product is put in solution. To the solution prepared in this manner, whose pH is about 7.3, 7 ml of a 1M solution of ferric chloride (7 mmol) is added and the pH of the solution is kept between 5 and 7 by adding N-methylglucamine. The solution immediately turns to an intense red color.

After the full amount of the second solution has been added, the pH of the solution is adjusted to a value between 6.8 and 7.2 by means of N-methylglucamine; it is diluted to 100 ml with water "for injection" and filtered through a 0.22μ filtering membrane under nitrogen pressure.

UV spectrum: lambda max. = 275 nm - epsilon 12300; lambda max. = 485 nm - epsilon 3780.

In a manner similar to that described in the preceding Examples 23–30, the complex compounds of all the compounds described in Examples 1 through 22 and listed in the tables on pages 48 through 52, are obtained with ferrous chloride, ferric chloride, gadolinium chloride, manganese chloride or with their carbonates or basic salts.

Table 1 lists data on the relaxation effectiveness and stability of some of the complexes according to the invention as compared with the complexes representing the current state of the art relative to the corresponding paramagnetic ion.

The symbols have the following meanings:
EDTA = Ethylene diamine tetra-acetic acid;
DTPA = Diethylene triamine penta-acetic acid
EHPG = Ethylene diamine-N,N'-bis-(2-(2-hydroxyphenyl)-acetic acid;
B 18950 = 3-phenylmethoxy-2-N-[2-N',N'-bis-(carboxymethyl)aminoethyl]-N-(carboxymethyl)-aminopropionic acid;
B 19030 = 3-phenylmethoxy-2-N-[2'-N'-[2''-N'',N''-bis-(carboxymethyl)-aminoethyl]-N'-(carboxymethyl)-aminoethyl]-N-(carboxymethyl)-aminopropionic acid;
B 19040 = N,N'-bis-(2-methoxy-1-carboxy-1-ethyl)-N,N'-bis-(2-hydroxyphenyl)-methyl)-ethylene diamine.

TABLE 1

STABILITY AND SPECIFIC RELAXIVITY* OF PARAMAGNETIC COMPOUNDS IN WATER AND IN RAT PLASMA - 20 MHz, 40° C.

| COMPLEX [M] | STABILITY CONSTANT OF THE COMPLEX (log. unit) | SPECIFIC RELAXIVITY (± standard deviation) $(mmol \cdot s)^{-1}.1$ | | RELATIVE** SPECIFIC RELAXIVITY | |
|---|---|---|---|---|---|
| | | IN WATER | IN PLASMA | IN WATER | IN PLASMA |
| Mn-EDTA | 14.0 | 3.63 (±0.10) | 5.29 (±0.04) | 1 | 1 |
| Mn-B 18950 | 13.4 | 2.98 (±0.11) | 8.18 (±0.32) | 0.82 | 1.55 |
| Gd-DTPA | 22.7 | 3.90 (±0.00) | 4.60 (±0.02) | 1 | 1 |
| Gd-B 19030 | 21.0 | 5.88 (±0.05) | 8.58 (±0.05) | 1.51 | 1.86 |
| Fe-EHPG | 33.9 | 1.07 (±0.04) | 1.35 (±0.04) | 1 | 1 |
| Fe-B 19040 | 37.1 | 1.03 (±0.01) | 1.40 (±0.03) | 0.96 | 1.04 |

*Expressed as the angular coefficient (b) of the regression line (y − a = bx) which correlates the rate of longitudinal relaxation (y) of the solution with the concentration of the paramagnetic complex (x). The line was calculated in the concentration interval between 0.1 and 5.0 mmol/l.
**Expressed as the ratio of the specific relaxivity of the claimed complex and the specific relaxivity of the corresponding reference complex.

From a comparison of the specific relaxivities (ratio of the effectiveness and the molar concentration of the complex), it is clear that substantial progress with respect to known compounds can be obtained in plasma with the manganese and gadolinium complexes of the invention.

While the effectiveness of the iron complex is not significantly different from that of the reference complex, its stability level is higher and it exhibits, moreover, important hepatotropic properties in animal experiments (rabbits).

This is indicated by the fact that excretion takes place to a large extent through the biliary system (55% excretion through the bile ducts versus 24% through the urinary tract in the first eight hours after I.V. administration). This result also agrees with the in vitro determination of the protein binding which, in rabbit plasma, is considerable, i.e., over 30%.

Fe-EHPG, a compound which represents the current state of the art in this particular field (Iron EHPG as an Hepatobiliary MR Contrast Agent: Initial Imaging and Biodistribution Studies, R. B. Lauffer et al,—Journal of Computer Assisted Tomography 9(3): 431–438 May- June 1985, Raven Press; New York) was tested under the same conditions and showed a decisively lower level of hepatotropism (biliary excretion 8%) and less protein binding, i.e., below 20%.

Some of the initial data on the tolerance of the complex compounds in question, as compared with non-complexed heavy metal ions, are set forth in Table 2.

TABLE 2

| Tolerance | DL 50 in mg/kg mouse | |
|---|---|---|
| | intravenous | oral |
| — · GdCl$_3$ | 72 (62–85) | |
| DTPA · Gd$^{(3+)}$ | 2628 (2448–2826) | |
| B 19030 · Gd$^{(3+)}$ | 3873 (3726–4026) | |
| — · MnCl$_2$ | 36 (31–40) | 1032 (965–1115) |
| EDTA · Mn$^{(2+)}$ | 767 (692–852) | 6650 (6127–7216) |
| B 18950 · Mn$^{(2+)}$ | 1177 (1089–1270) | 8329 (7631–9074) |

Explanation

B 19030.Gd$^{(3+)}$=N-methyl-D-glucamine salt
DTPA.Mn$^{(2+)}$=N-methyl-D-glucamine salt
B 18950.Mn$^{(2+)}$=N-methyl-D-glucamine, Example 25.

Table 2 shows that by complexing paramagnetic heavy metal ions with polyamino-polycarboxylic acids according to the invention, substantial detoxification is obtained and relatively tolerable complex heavy metal compounds are formed.

This demonstrates that the complex heavy metal compounds of the invention according to formula I are endowed with the necessary characteristics of contrast-enhancing agents for nuclear spin tomography imaging.

We claim:

1. A compound having the formula

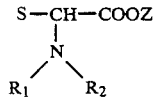

wherein:
S is the group —A—O—R wherein;
A is —(CH$_2$)$_m$—; —CH$_2$—C—(CH$_3$)$_2$—;
m is an integer from 1 to 5;
R is H; linear or branched alkyl of 1 to 8 carbon atoms, said carbon atoms being unsubstituted or substituted by one or more hydroxy group; aralkyl of 1 to 4 aliphatic carbon atoms; phenyl or phenyl substituted by halogen, amino or hydroxy; (poly)-oxa-alkyl of 1 to 10 oxygen atoms and from 3 to 30 carbon atoms;
R$_1$ is —CH$_2$COOZ; —CH(CH$_3$)COOZ; —(CH$_2$)$_n$—N(CH$_2$COOZ)$_2$; hydroxy-arylalkyl radical, in which the aryl radical is unsubstituted or substituted by hydroxy;
R$_2$ is —CH$_2$COOZ; —CH(CH$_3$)COOZ;

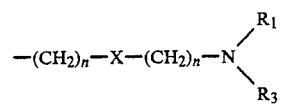

wherein
R$_3$ is —CH$_2$COOZ; —CH(CH$_3$)COOZ; a monovalent radical having the structure

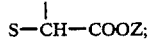

X is a direct chemical bond; —O—; —S—; —NH—;

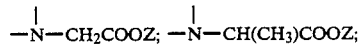

n is the integer 2 or 3, with the proviso that when X is a direct chemical bond, n is 1, 2 or 3;
Z is H or a negative charge.

2. A substituted α-amino propionic acid of formula

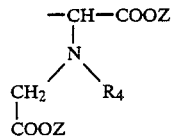

wherein:
 is:
(1) —CH$_2$OR$_5$;
(2) —C(CH$_3$)$_2$—CH$_2$OR$_5$;
wherein R$_5$ is
(a) phenyl;
(b) benzyl;
(c) 1–8 carbon alkyl;
(d) dihydroxy substituted lower alkyl;
(e) —H;
(f) —(OCH$_2$—CH$_2$)$_p$CH$_3$
wherein p is an integer number between 1 and 5;
and R$_4$ is —(CH$_2$)$_n$—X—(CH$_2$)$_n$—N(CH$_2$COOZ)$_2$
wherein X is:
(a) a direct chemical bond;
(b) —O—;

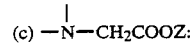

and n is 1, 2 or 3 when X is a direct bond or the integer is 2 or 3 and Z is H or a negative charge.

3. A substituted α-amino propionic acid of formula

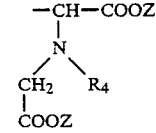

wherein  is —CH$_2$—OR$_5$ wherein R$_5$ is:
(a) benzyl;
(b) —CH$_2$—CH$_2$—phenyl;
(c) lower alkyl of 1–3 carbon atoms;
(d) H;
and R$_4$ is

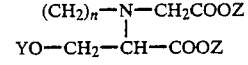

wherein Y is:
(1) benzyl;

(2) —CH₂—CH₂—phenyl:
(3) lower alkyl of 1 to 3 carbon atoms;
(4) H

X is
 (a) a direct chemical bond;
 (b) —O—;

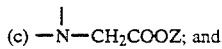

n is 1 when X is a direct chemical bond or 2 when X is (b) or (c);

Z is H or a negative charge.

4. A substituted α-amino propionic acid of formula

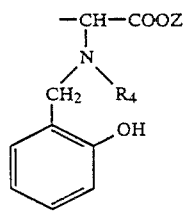

wherein:
 is —CH₂—O—R₅; —C(CH₃)₂—CH₂—O—R₅;
 wherein R₅ is
 (a) H;
 (b) lower alkyl of 1 to 3 carbon atoms;
 (c) dihydroxy substituted lower alkyl;
 (d) (CH₂CH₂O)₁₋₅CH₃;

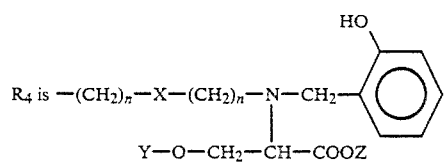

wherein Y is
 (a) H;
 (b) lower alkyl (1-3 carbon atoms);
 (c) dihydroxysubstituted lower alkyl;
 (d) (CH₂CH₀O)₁₋₅CH₃;

X is
 (a) a direct chemical bond;
 (b) —O—;

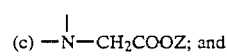

n is 1 when X is (a) or 2 when X is (b) or (c);
and Z is H or a negative charge.

5. A substituted α-amino propionic acid of formula

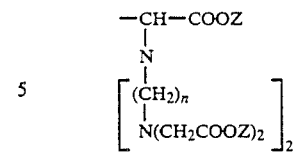

wherein:
 is —CH₂—O—R₅; —C(CH₃)₂—CH₂—O—R₅;
 wherein R₅ is
 (a) lower alkoxy of 1 to 3 carbon atoms;
 (b) benzyl;
 (c) (CH₂CH₂O)₁₋₅CH₃;

n is the integer 1 or 2;
Z is H or a negative change.

6. The compound according to claim 1 wherein

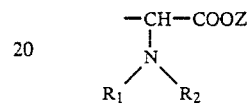

is selected from the group consisting of
 3-hydroxy-2-N[2'-N'-[2''-N'',N''-bis-(carboxymethyl)-aminoethyl]-N'-(carboxymethyl)-aminoethyl]-N-(carboxymethyl)-amino-propionic acid
 3-phenylmethoxy-2-N-[2'N'-[2''-N'',N''-bis-(carboxymethyl)-aminoethyl[-N'-(carboxymethyl)-aminoethyl]-N-(carboxymethyl)-aminopropionic acid,
 3-methoxy-b 2-N,N-bis-[2'-N,N'-bis-(carboxymethyl)-aminoethyl]aminopropionic acid,
 3-phenylmethoxy-b 2-N,N-bis-[2'-N',N'-bis(carboxymethyl)-aminoethyl]aminopropionic acid,
 4-(3,6,9,12,15-pentaoxahexadecyloxy)-3,3-dimethyl-b 2-N[2'-N'-[2''-N'',N''-bis-(carboxymethyl)-aminoethyl]-N,-carboxymethyl)-aminoethyl-N-(carboxymethyl)-amino-butric acid,
 4-(3,6,9,12,15-pentaoxahexadecyloxy)-3,3-dimethyl-b 2-N, N-bis-[2'-N,,N'-bis-(carboxymethyl)-aminoethyl]-amino-butryic acid,
 3-hydroxy-b 2-N-[2'-N',N'-bis-(carboxymethyl)-aminoethyl]-N-(carboxymethyl)-amino-propionic acid,
 3-phenylmethoxy-b 2-N-[2'-N',N'-bis-(carboxymethyl)-aminoethyl]-N-(carboxymethyl)-amino-propionic acid,
 3-octyloxy-b 2-N-[2'-N',N'-bis-(carboxymethyl)-aminoethyl]-N-(carboxymethyl)-amino-propionic acid,
 N,N'-bis-(2-hydroxy-1-carboxy-1-ethyl)-N,N'-bis-(carboxymethyl)ethylene diamine,
 4-methoxy-3,3-dimethyl-b 2-N-[2'-N',N'-bis-(carboxymethyl)-aminoethyl]-N-(carboxymethyl)-aminobutyric acid,
 3-phenylmethoxy-b 2-N-[2-[2-N',N'-bis-(carboxymethyl)-aminoethyoxy]ethyl]-N-(carboxymethyl)aminopropionic acid,
 N,N'-bis-(2-methoxy-1-carboxyl-1-ethyl)-N,N'-bis-(2-hydroxy phenylmethyl)-ethylene diamine,
 N,N'-bis-(3,6,9,12-tetraoxa-1-carboxy-1-tridecyl)-N,N'-bis-(2-hydroxy-phenylmethyl)-ethylene diamine,
 N,N'-bis-(3-methoxy-2,2-dimethyl-1-carboxy-1-propyl-N,N-bis-(2-hydroxy-phenylmethyl)-ethylene diamine,
 N,N'-bis-3-(2,3-dihydroxypropoxhy)-2,2-dimethyl-1-carboxy-1-propyl)-N,N'-bis-(2-hydroxy-phenylmethyl)-ethylene diamine.

* * * * *

UNITED STATES PATENT AND TRADEMARK OFFICE
CERTIFICATE OF CORRECTION

PATENT NO. : 4,980,502                           Page 1 of 3

DATED : December 25, 1990

INVENTOR(S) : Ernest Felder, et al

It is certified that error appears in the above-indentified patent and that said Letters Patent is hereby corrected as shown below:

Column 38, Claims 2 and 3, lines 18-22 and 50-54, the formulas should read as follows:

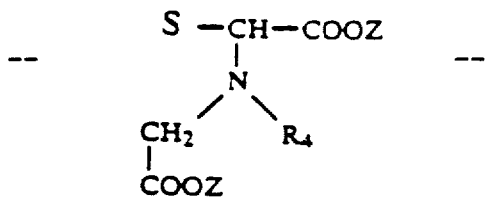

Column 38, line 25, should read -- S is: --; and
   line 56, should read --wherein S is $-CH_2-OR_5$ wherein $R_5$ is:--.

Column 39, Claim 4, lines 22-28, the formula should read as follows:

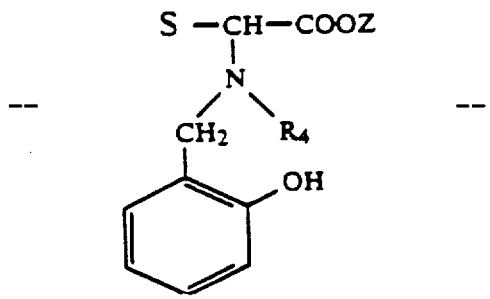

Column 39, line 32, should read

-- S is $-CH_2-O-R_5$; $-C(CH_3)_2-CH_2-O-R_5$; --.

UNITED STATES PATENT AND TRADEMARK OFFICE
CERTIFICATE OF CORRECTION

PATENT NO. : 4,980,502

DATED : December 25, 1990

INVENTOR(S) : Ernest Felder, et al

It is certified that error appears in the above-indentified patent and that said Letters Patent is hereby corrected as shown below:

Column 40, Claim 5, lines 2-7, the formula should read as follows:

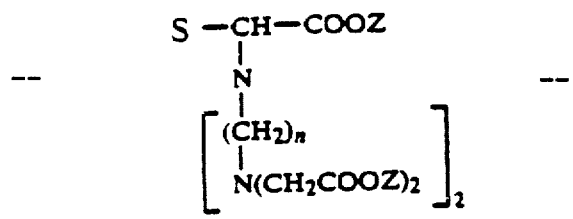

Column 40, line 10, should read

-- S is $-CH_2-O-R_5$; $-C(CH_3)_2-CH_2-O-R_5$; --.

UNITED STATES PATENT AND TRADEMARK OFFICE
CERTIFICATE OF CORRECTION

PATENT NO. : 4,980,502
DATED : December 25, 1990
INVENTOR(S) : Ernest Felder, et al It is certified that error appears in the above-indentified patent and that said Letters Patent is hereby corrected as shown below:

Column 40, Claim 6, lines 19-22, the formula should read as follows:

-- 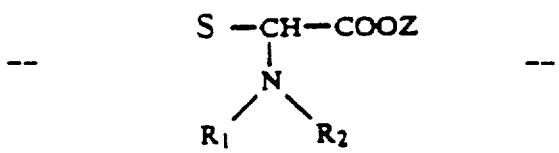 --

Signed and Sealed this

Second Day of November, 1993

Attest:

BRUCE LEHMAN

Attesting Officer     Commissioner of Patents and Trademarks